(12) United States Patent
Garrell et al.

(10) Patent No.: US 9,175,026 B2
(45) Date of Patent: Nov. 3, 2015

(54) SYNTHESIS OF THIOETHER CONTAINING TRIALKOXYSILANES

(75) Inventors: Robin L. Garrell, Los Angeles, CA (US); Alexander K. Tucker-Schwartz, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 253 days.

(21) Appl. No.: 14/001,096

(22) PCT Filed: Mar. 22, 2012

(86) PCT No.: PCT/US2012/030080
§ 371 (c)(1),
(2), (4) Date: Aug. 22, 2013

(87) PCT Pub. No.: WO2012/129380
PCT Pub. Date: Sep. 27, 2012

(65) Prior Publication Data
US 2013/0345412 A1    Dec. 26, 2013

Related U.S. Application Data

(60) Provisional application No. 61/466,816, filed on Mar. 23, 2011.

(51) Int. Cl.
| | | |
|---|---|---|
| *C07F 7/08* | (2006.01) | |
| *C23C 16/00* | (2006.01) | |
| *C07F 19/00* | (2006.01) | |
| *C07F 7/18* | (2006.01) | |
| *B05D 1/18* | (2006.01) | |
| *B82Y 30/00* | (2011.01) | |
| *B82Y 40/00* | (2011.01) | |
| *B05D 1/36* | (2006.01) | |

(52) U.S. Cl.
CPC .............. *C07F 19/00* (2013.01); *B05D 1/185* (2013.01); *B82Y 30/00* (2013.01); *B82Y 40/00* (2013.01); *C07F 7/08* (2013.01); *C07F 7/1876* (2013.01); *C07F 7/1892* (2013.01); *B05D 1/36* (2013.01); *C23C 16/00* (2013.01)

(58) Field of Classification Search
CPC .................................. C07F 7/08; C23C 16/00
USPC ........................... 556/427; 427/489, 588, 593
See application file for complete search history.

(56) References Cited

U.S. PATENT DOCUMENTS

| | | |
|---|---|---|
| 3,170,940 A | 2/1965 | Johnston |
| 4,366,307 A | 12/1982 | Singh et al. |
| 4,611,892 A | 9/1986 | Kawashima et al. |
| 5,618,898 A | 4/1997 | Nagasawa et al. |
| 2009/0287015 A1 | 11/2009 | Biteau et al. |

FOREIGN PATENT DOCUMENTS

DE    2221349    12/1972

OTHER PUBLICATIONS

Supplementary European Search Report from EP Patent Application No. 12760785.1 dated Oct. 15, 2014.
J. Scott Parent et al., "Terminal Functionalization of Polypropylene by Radical-Mediated Thiol-Ene Addition", Macromolecules, vol. 38, No. 13, pp. 5538-5544, 2005.
Dietrich Braun "Origins and Development of Initiation of Free Radical Polymerization Processes", International Journal of Polymer Science, vol. 201, No. 17, pp. 1-10, 2009.
Alexander K. Tucker-Schwartz et al., "Thiol-ene Click Reaction as a General Route to Functional Trialkoxysilanes for Surface Coating Applications", Journal of the American Chemical Society, vol. 133, No. 29, pp. 11026-11029, 2011.
Thierry Materne "Organosilane Technology in Coating Applications: Review and Perspectives", Retrieved from the Internet: http://www.dowcorning.com/content/publishedlit/26-1402-01.pdf, 2006.
Lowe et al. "Thiol-ene click reactions and recent applications in polymer and materials synthesis", Polymer Chemistry, vol. 1, No. 1, pp. 17-36, 2009.
PCT International Search Report and Written Opinion dated Oct. 18, 2012 for PCT Application No. PCT/US2012/030080.

*Primary Examiner* — Elvis O Price
(74) *Attorney, Agent, or Firm* — Gates & Cooper LLP

(57) ABSTRACT

The invention relates to a radical-initiated thiol-ene or thiol-yne "click" reaction that provides a simple and efficient route to diverse trialkoxysilanes. Trialkoxysilanes made in this way are obtained in quantitative to near-quantitative yields with high purity without any or minimal purification. A wide range of functional groups is tolerated in this approach, and even complex alkenes click with the silane precursors. The modular nature of these radical-based thiol-ene or thiol-yne "click" reactions allows a wide variety of pendant groups to be coupled to silane compounds that can then be coupled to a wide variety surfaces in order to modify their material properties. Consequently, such radical initiated thiol-ene and thiol-yne reactions provide facile and efficient methods for preparing an enormous number of surface-active functional trialkoxysilanes.

20 Claims, 26 Drawing Sheets

Synthesis of triethoxysilanes via photoinitiated thiol-ene reactions between MPTES and various alkenes.[a]

| Alkene | Triethoxysilane | | Conv. (%)[b] | Purity (%)[c] |
|---|---|---|---|---|
| allyl-O-(CH2CH2O)4-CH3 | (EtO)3Si-(CH2)3-S-(CH2)2-O-(CH2CH2O)4-CH3 | 1 | >99 | 96 |
| allyl-O-CH2CH2-(4-methylthiazole) | (EtO)3Si-(CH2)3-S-(CH2)3-O-CH2CH2-(4-methylthiazole) | 2 | >99 | 95 |
| CH2=CH-CH(OEt)2 | (EtO)3Si-(CH2)3-S-(CH2)2-CH(OEt)2 | 3 | >99 | 96 |
| CH2=CH-(CH2)7-C(O)-Ot-Bu | (EtO)3Si-(CH2)3-S-(CH2)7-C(O)-Ot-Bu | 4 | 98 | 96 |
| allyl-NH-C(S)-NH2 | (EtO)3Si-(CH2)3-S-(CH2)3-NH-C(S)-NH2 | 5 | >99[e] | 95 |
| Boc-Hyp(O-pentenoyl)-OMe | (EtO)3Si-(CH2)3-S-(CH2)4-C(O)-O-Hyp(Boc)-OMe | 6 | 96 | 94 |
| pentenoyl-NH-quinuclidine | (EtO)3Si-(CH2)3-S-(CH2)7-C(O)-NH-quinuclidine | 7 | 98[d] | 96 |
| quinine (vinyl) | (EtO)3Si-(CH2)3-S-quinine | 8 | 98[d] | 96 |
| pentenoyl-Ser(OtBu)-N(CH2CO2tBu)2 | (EtO)3Si-(CH2)3-S-(CH2)4-C(O)-O-Ser(OtBu)-N(CH2CO2tBu)2 | 9 | 94[f] | 90 |
| allyl-O-(per-OAc mannose) | (EtO)3Si-(CH2)3-S-(CH2)3-O-(per-OAc mannose) | 10 | >99[d] | 97 |

FIG. 2

Synthesis of trimethoxysilanes and triethoxysilanes via photoinitiated thiol-ene reaction between MPTMS/alkenes or ATES/thiols.

| Alkene | Trialkoxysilane | | Conv. (%)[c] | Purity (%)[d] |
|---|---|---|---|---|
| (allyl diethyl acetal structure) OEt, OEt | (MeO)₃Si-(CH₂)₃-S-CH₂CH₂-CH(OEt)₂ | 11 | >99[a] | 96 |
| CH₂=CH-(CH₂)₇-COOH | (MeO)₃Si-(CH₂)₃-S-(CH₂)₉-COOH | 12 | >99[a,e] | 96 |
| HS-CH₂-C₆H₅ | (EtO)₃Si-(CH₂)₃-S-CH₂-C₆H₅ | 13 | >99[b] | 97 |
| HS-CH₂-CH(NHBoc)-C(O)OMe | (EtO)₃Si-(CH₂)₃-S-CH₂-CH(NHBoc)-C(O)OMe | 14 | >99[b] | 97 |

FIG. 3

Scheme of thiol-ene reaction mechanism for the synthesis of functional trialkoxysilanes.

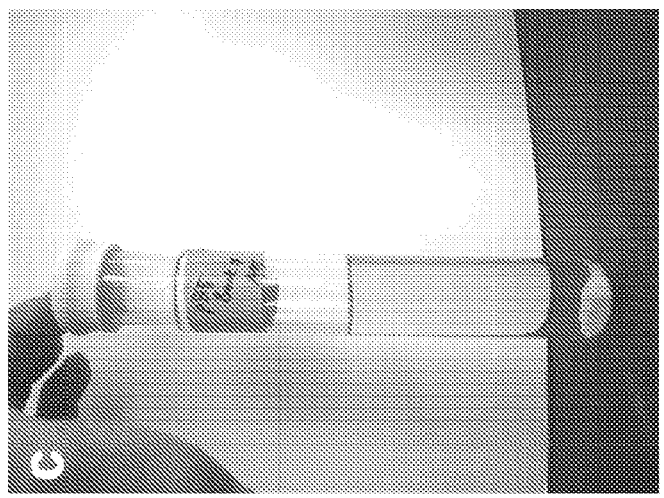
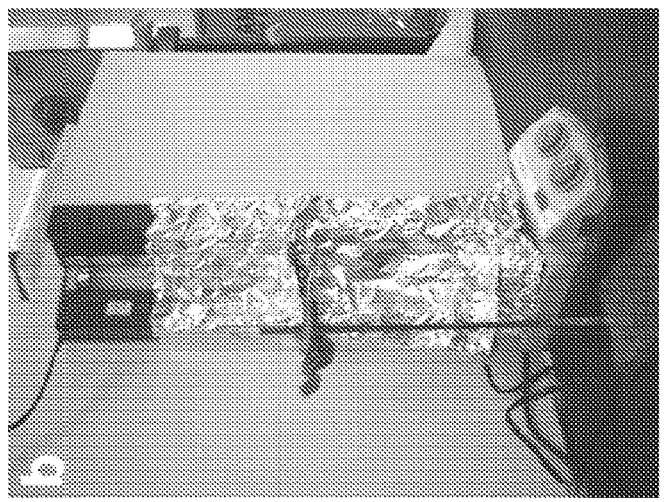
FIG. 7

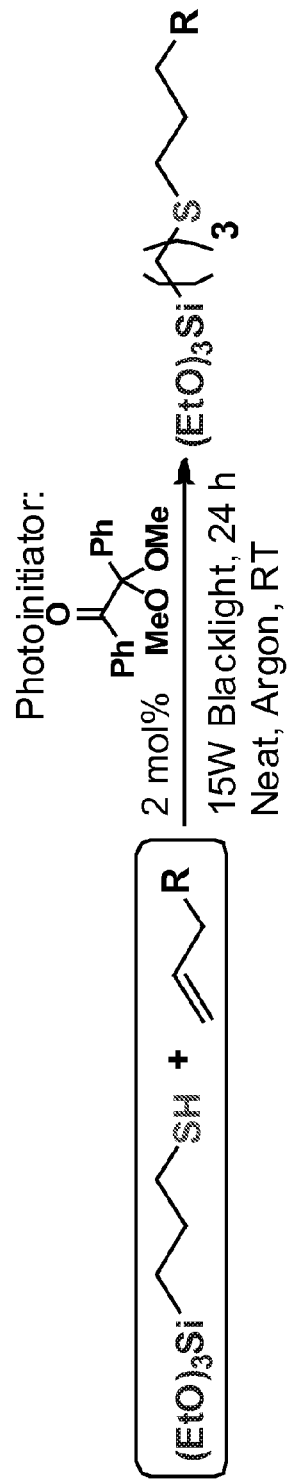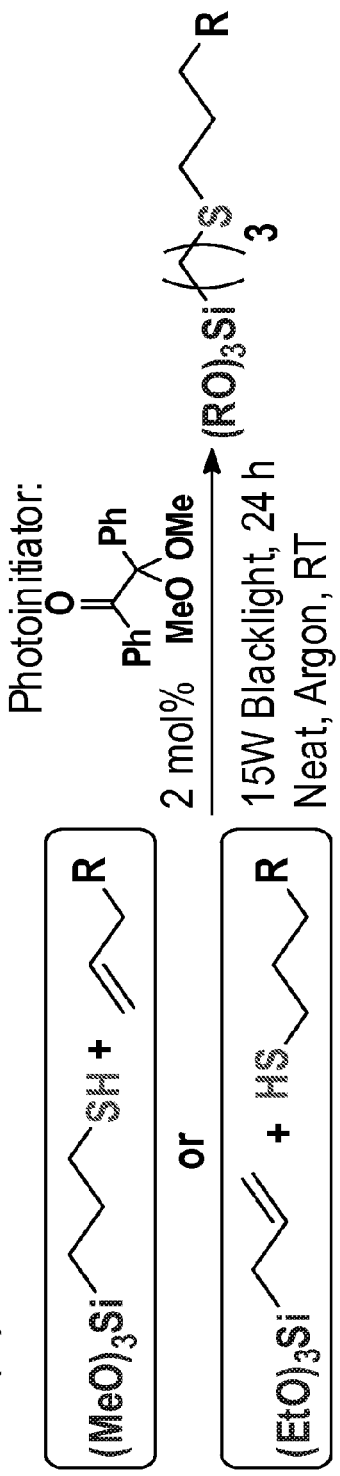
FIG. 14

Initiators:

$$\underset{A}{\underset{\text{Ph}}{\overset{\text{O}}{\|}}\text{C}(\text{Ph})(\text{OMe})(\text{OMe})} \quad \underset{B}{\underset{\text{Ph}}{\overset{\text{O}}{\|}}\text{C}-\text{Ph}} \quad \underset{C}{\text{NC}-\text{C}(\text{Me})_2-\text{N}=\text{N}-\text{C}(\text{Me})_2-\text{CN}} \quad \underset{D}{\text{Et}_2\text{B}-\text{Et}}$$

$$(\text{RO})_3\text{Si}\diagdown\diagdown\diagdown\text{SH} \; + \; \diagup\diagdown\text{R} \quad \xrightarrow[\text{UV light, solvent}]{X \text{ mol\% initiator}} \quad (\text{RO})_3\text{Si}\diagdown\diagdown\diagdown\text{S}\diagdown\diagdown\text{R}$$
1 equiv      1 equiv      temp., time Thiol-ene reactions with alkene functionalized 2-thiophenemethanol under different reaction conditions.

| Alkene | Initiator | mole % | Solvent | UV | Argon | Time | Temp. | Conv. [%] | Purity [%] |
|---|---|---|---|---|---|---|---|---|---|
| thiophene-CH₂-O-allyl | A | 2.0 | -- | 15 W | + | 24 h | RT | 73 | -- |
| thiophene-CH₂-O-allyl | A | 2.0 | -- | 100 W (~8 in) | + | 24 h | RT | 84 | -- |
| thiophene-CH₂-O-allyl | B | 5.0 | -- | 15 W | + | 24 h | RT | 81 | -- |
| thiophene-CH₂-O-allyl | C | 5.0 | Dry toluene (200 μL) | -- | + | 25 h | 80°C | >90% | -- |
| thiophene-CH₂-O-allyl | D | 10.0 | -- | -- | ++ | 24 h | RT | 52 | -- |
| thiophene-CH₂-O-C(O)-butenyl | D | 10.0 | -- | -- | ++ | 24 h | RT | 41 | -- |
| thiophene-CH₂-O-C(O)-butenyl | D | 10.0 | -- | -- | ++ | 48 h | RT | >99 | 95 |
| thiophene-CH₂-O-C(O)-butenyl | A | 2.0 | -- | 15 W | + | 24 h | RT | >99 | 95 |
| thiophene-CH₂-O-C(O)-butenyl | C | 5.0 | Dry toluene (200 μL) | -- | + | 24 h | 80°C | | |

*FIG. 19*

SYNTHESIS OF THIOETHER CONTAINING TRIALKOXYSILANES

REFERENCE TO RELATED APPLICATIONS

This application claims the benefit under 35 U.S.C. Section 119(e) of and commonly-assigned U.S. Provisional Patent Application Ser. No. 61/466,816, filed on Mar. 23, 2011, entitled "SYNTHESIS OF THIOETHER CONTAINING TRIALKOXYSILANES", the contents of which are incorporated herein by reference.

STATEMENT OF GOVERNMENT SUPPORT

This invention was made with Government support under Grant No. DGE-0654431, awarded by the National Science Foundation. The Government has certain rights in this invention.

FIELD OF THE INVENTION

This invention is in the field of synthetic chemistry, in particular methods for making and using trialkoxysilanes that include thioether linkages.

BACKGROUND OF THE INVENTION

The ability to modify the physical and chemical properties of surfaces and interfaces is important in fundamental and applied materials science. One of simplest and most common methods is to react trialkoxy- or trichlorosilanes with hydroxylated surfaces, such as metal oxides. Silanes form strong covalent oxane bonds to such surfaces, making them particularly useful for bridging the inorganic and organic components. For these reasons, silane compounds are used to prepare many important materials and devices, including catalyst-coated magnetic and mesoporous metal oxides (see, e.g., Shylesh, S., et al. *Angew. Chem., Int. Ed. Engl.* 2010, 49, 3428-3459), superhydrophobic surfaces (see, e.g., Crick, C. R., et al. *Chem.-Eur. J.* 2010, 16, 3568-3588), organic photovoltaics (see, e.g. Valentini, L., et al. *Carbon* 2010, 48, 861-867), thin-film transistors (see, e.g., LeMieux, M. C., et al., *Science* 2008, 321, 101-104), and sensors (see, e.g., Melde, B. J., et al. *Sensors* 2008, 8, 5202-5228) to name a few.

Conventional reactions commonly used to produce mono-, di-, and trialkoxysilanes include hydrosilylation of alkenes and alkynes, nucleophilic substitution reactions, and reactions of amines and alcohols with isocyanate-containing trialkoxysilanes. Conventional hydrosilylation of alkenes and alkynes utilizes triethoxy-, trimethoxy-, or methyldimethoxysilane and a platinum catalyst, with or without ligands (see, e.g., Alonso, J. M., et al. *Langmuir* 2008, 24, 448-457; Kim, Y. J., et al. *Langmuir* 2010, 26, 7555-7560; Sabourault, N., et al. *Org. Lett.* 2002, 4, 2117-2119; Uccello-Barretta, G., et al. *J. Organomet. Chem.* 2008, 693, 1276-1282). Nucleophilic substitution reactions rely on a nucleophilic attack of ligands on 3-halopropyltrimethoxy- or triethoxysilanes (see, e.g., Abu-Reziq, R., et al. *Adv. Synth. Catal.* 2007, 349, 2145-2150; Dalaigh, C. O., et al. *Org. Biomol. Chem.* 2006, 4, 2785-2793; Guo, Z. M., et al. *Chem. Commun.* 2006, 4512-4514). Reactions of amines and alcohols with isocyanate-containing trialkoxysilanes rely on reactions of amines and alcohols with 3-isocyanatopropyltrimethoxy- or triethoxysilane (see, e.g., Cui, Y. J., et al. *Dyes Pigments* 2008, 77, 217-222; Shiels, R. A., et al. *Adv. Synth. Catal.* 2008, 350, 2823-2834; Wu, Y. P., et al. *Nanoscale Res. Lett.* 2009, 4, 738-747). Other reactions have relied on reductive amination between 3-aminoproyltriethoxysilane and a ketone, using sodium borohydride as the reducing agent or thermal or photoinitiated radical thiol-ene chemistry to make a small amount of a single silane with either an alkene modified N,N-dimethylpyridine or terpyridine pendant functional group (see, e.g., Rissing, C., et al. *Organometallics* 2009, 28, 3167-3172; Killops, K. L., et al. *J. Am. Chem. Soc.* 2008, 130, 5062). Of the various methods used to form trialkoxysilane compounds that are known in the art, hydrosilylation is the most widely used because of typically good product yields, a ready availability of the metal catalysts, and a low cost of the trialkoxysilane precursors.

Unfortunately, all conventional methodologies for synthesizing trialkoxysilanes have significant drawbacks and limitations. For example, even though hydrosilylation reactions (e.g., hydrosilylation of alkenes and alkynes with triethoxy-, trimethoxy-, or methyldimethoxysilane) can provide good product yields, they typically require expensive metal catalysts (e.g., palladium catalysts) and/or chiral organic ligands. Hydrosilylation reactions are problematical due to their limited functional group tolerance (e.g., such reactions are not tolerant of ally esters, amides, and metal chelating functional groups), the fact that such reactions are limited to specific reaction conditions that depend on the palladium catalyst used, and further are not completely regioselective. In addition, hydrosilylation reactions can require the use of excess reagents and further require post-synthetic purification to remove metals, contaminants, and excess reactants from the moisture-sensitive products. Other conventional methodologies for synthesizing trialkoxysilanes including nucleophilic attack of ligands on 3-halopropyltrimethoxy- or triethoxysilanes, reactions of amines and alcohols with 3-isocyanatopropyltrimethoxy- or triethoxysilane, and reductive amination between 3-aminoproyltriethoxysilane and with ketones, have even more limited functional group tolerance, and are therefore limited in substrate scope, and have relatively poor product yields. Moreover, with the exception of a single hydrosilylation methodology using $PtO_2$, which has been demonstrated to work on a large scale (see, e.g., Sabourault, N., et al. *Org Lett* 2002, 4, 2117-2119), all of the current methodologies listed above have only been shown to produce silanes on an approximately 1-10 mmol scale. In addition, these methodologies are also often non-quantitative, which necessitate tedious purification of the moisture sensitive compounds. As a result, although many simple and complex trialkoxysilanes can be made by conventional methods and are currently available on the commercial and retail market, a large number of them are very expensive due to their problematical synthesis regimes.

There is a need in the art for simple and inexpensive methods for producing a wide variety of desirable trialkoxysilane compounds in a relatively pure form. Additionally, there is a need for a simple way to make tailored silanes, in order to, for example, design and produce materials and devices having properties specifically selected for a wide variety of applications or that are amenable to further chemical modifications. At the same time, such processes should be environmentally friendly and not require the use of large amount of hazardous materials (e.g., solvents etc.). The invention disclosed herein addresses such needs while overcoming many of the drawbacks and disadvantages of conventional methodologies.

SUMMARY OF THE INVENTION

The invention disclosed herein provides simple and efficient methods for making trialkoxysilane thioether compounds that include one or more functional groups, methods for using these compounds, as well as materials and devices that incorporate such compounds. Embodiments of the invention include methods falling within the class of modular addition or "click" reactions, and in particular involve the addition of one thiol across an alkene or two thiols across an alkyne. These thiol-ene/thiol-yne reactions tolerate the addition of many functional groups, can be run neat or in benign solvents such as water, and provide quantitative or near-quantitative yields. In addition, embodiments of the invention can be used to produce highly pure products in the vessel in which they are synthesized and consequently require little or no purification. With such attributes, embodiments of the invention are particularly well suited for making trialkoxysilanes that are coupled to functional groups selected to have specific material and/or chemical and/or biological properties. Such compounds can then be utilized in a multitude of applications, for example, to coat and modify the material properties of a wide variety of surfaces.

While trialkoxysilanes are widely used to create or functionalize surfaces, there are relatively few methods for synthesizing functional trialkoxysilanes. In this context, a significant advantage of embodiments of the present invention is that they allow the synthesis of trialkoxysilanes that are covalently coupled to a wide variety of function groups. The modularity of the present invention provides artisans with an enormous amount of flexibility when designing and synthesizing tailored, functional trialkoxysilanes. For this reason, compounds made by embodiments of the invention can be used, for example, to form a variety of surfaces having selected properties (e.g., the surfaces of nanoparticles). Consequently, compounds made by embodiments of the invention can be adapted for use in diverse technologies including chemical and biological sampling systems, diagnostic devices, and drug delivery vehicles.

The invention disclosed herein has a number of embodiments. One illustrative embodiment is a method for making a trialkoxysilane compound comprising a thioether by forming a mixture comprising a trialkoxysilane compound, a compound comprising a sulfhydryl moiety, an alkene compound or an alkyne compound, and a radical initiator agent. In this embodiment, the mixture is then subjected to conditions that initiate a chemical reaction in the mixture so that the trialkoxysilane compound comprising the thioether is made. Typically these conditions involve modulating the activity of the radical initiator agent by exposing the mixture to light, heat or oxygen. In an illustrative embodiment of the invention, the radical initiator agent is modulated by exposure to light, a condition that allows it to react with a hydrogen atom in a first sulfhydryl moiety so as to form a thiyl radical. In this embodiment, the thiyl radical reacts with the alkene or the alkyne so as to form a radical intermediate; and the radical intermediate then reacts with a hydrogen atom in a second thiol moiety to complete formation of a thioether bond, with a consequence of this reaction being the formation of the trialkoxysilane compound comprising the thioether. Subsequently, the newly formed thiyl radical undergoes the same process with another alkene or alkyne. Optionally in such embodiments, the activity of the radical initiator agent is initiated by ultraviolet light and the mixture is contained in an optically transparent vessel.

In embodiments of the invention, the components of the reaction mixtures and/or the reaction conditions can be controlled so as to control the characteristics of the product produced by such processes (e.g., the purity of that product). For example, in some embodiments of the invention, the components of the reaction mixture and/or the reaction conditions are controlled so as the reaction produces a composition of matter wherein the trialkoxysilane compound comprising the thioether has a high degree of purity, for example is at least 90% pure. In typical embodiments of the invention, the amount of the constituents can be controlled so that the mixture comprises 1:1 molar equivalents of a sulfhydryl moiety and an alkene. In some embodiments of the invention, the amount constituents can be controlled so that the mixture comprises 2:1 molar equivalents of a sulfhydryl moiety and an alkyne.

In typical embodiments of the invention, the chemical reaction is performed as a one-pot synthesis. Optionally, the mixture does not comprise a metallic catalyst agent or a chiral organic ligand. In some embodiments of the invention, the mixture comprises less than 5 weight percent of a solvent. In certain embodiments of the invention, the mixture does not comprise any solvent. Optionally, the reaction is performed in the presence of an inert gas such as $N_2$. Certain embodiments of the invention can further comprise placing the composition of matter under a negative pressure to remove a constituent of the composition of matter having a vapor pressure higher than the trialkoxysilane compound comprising the thioether (e.g., a solvent, a byproduct or the like).

Another embodiment of the invention is method for modifying a surface of a material by using a compound generated by a process disclosed herein to couple one or more functional groups to that material. In such methods, the silane groups on the compounds are relied upon for their ability to be easily grafted onto many types of surfaces and the functional group on the compounds are relied upon for their ability to modify a material property of such surfaces. In this context, embodiments of the processes disclosed herein are relied upon to join the silane group and the functional group together via thioether bonds, bonds which are known to provide a strong covalent linkage. Embodiments of the invention include a first step of making a trialkoxysilane compound comprising a thioether by forming a mixture comprising a trialkoxysilane compound, a compound comprising a sulfhydryl moiety, an alkene compound or an alkyne compound, and a radical initiator agent. In this method, the mixture is then subjected to conditions that initiate a chemical reaction in the mixture so that the trialkoxysilane compound comprising the thioether is made. Following this synthesis of the trialkoxysilane compound comprising the thioether, this compound it then coupled to the surface of a material so that the surface of the material is modified. In an illustrative embodiment of the invention, the surface is hydroxylated and the trialkoxysilane compound comprising the thioether is covalently coupled to the surface via an oxane bond.

Optionally in such embodiments of the invention, the alkene, the alkyne or the compound comprising a sulfhydryl moiety is covalently linked to a pendant group comprising one or more functional groups such as an imaging agent, a surface wetting agent, a water repelling agent, a lipophilic agent, a coupling agent, a chelating agent, a cell-binding agent, a biomolecule-binding agent, a polymer-binding agent, a particle binding agent, an antimicrobial agent, a therapeutic agent, a ligand or a catalytic agent, so that the surface is modified by having the functional group coupled thereto. In illustrative embodiments of the invention, the surface to which the compound is coupled comprises a metal composition, an oxide composition, a polymer composition, a silicone composition or a plastic composition that is, for example, part of a functional material or apparatus such as a nanoparticle, a microparticle, a membrane, a chromatographic matrix, a porous monolith, a sensor, a microfluidic device, a piezoelectric device, a silicon or glass chip, a catalyst support, an electrode, a micro-electrical mechanical device or a light emitting device. Embodiments of the invention further include a material, a matrix, a substrate, a particle, a device or the like having a surface modified according to the methods disclosed herein.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 2 is a table illustrating the synthesis of triethoxysilanes via photoinitiated thiol-ene reactions between MPTES and various alkenes. With regards to the superscripts—(a): A dry 10 mL round bottom was charged with 1 equiv. alkene (0.4-5.0 mmol), 1 equiv. MPTES (0.4-5.0 mmol), and 2 mol % Irgacure® 651, back filled with argon, and irradiated for 24 to 27 h with a 15 W blacklight ($\lambda_{max}$=346 nm). (b): Quantified by $^1$HNMR. (c): Determined by gas chromatography/mass spectrometry (GC/MS) or 1HNMR. (d): Dry CHCl$_3$ (0.25-1.0 mL) added to solvate alkene. (e): Dry MeOH (0.6 mL) added to solubilize the alkene. (f): Reaction mixture irradiated 45 h with 3 mol % Irgacure®651, then an additional 22 h after addition of another 2 mol % Irgacure®651. High solution viscosity and UV absorption by forming product 9 reduced substrate conversion.

FIG. 3 is a table illustrating the synthesis of trimethoxysilanes and triethoxysilanes via photoinitiated thiol-ene reaction between MPTMS/alkenes or ATES/thiols. With regards to the superscripts—(a): A dry 10 mL round bottom was charged with 1 equiv. alkene (2.0-2.5 mmol), 1 equiv. MPTMS (2.0-2.5 mmol), and 2 mol % Irgacure® 651, back filled with argon, and irradiated for 24 vh with a 15 W blacklight ($\lambda_{max}$=346 nm). (b): A dry 10 mL round bottom was charged with 1 equiv. thiol (2.0-2.5 mmol), 1 equiv. 3-mercaptopropyltriethoxysilane (2.0-2.5 mmol), and 2 mol % Irgacure® 651, back filled with argon, and irradiated for 24 h with a 15 W blacklight ($\lambda_{max}$=346 nm). (c): Quantified by $^1$HNMR. (d): Determined by gas chromatography/mass spectrometry (GC/MS) or $^1$HNMR. (e): Dry CHCl$_3$ (0.5 mL) added to solubilize alkene.

FIG. 7 is a collection of images of an illustrative setup for large-scale synthesis of product 3: a) prior to, and b) during reaction; c) image of a reaction tube containing product 3 after the reaction was complete.

FIG. 14 comprises schematics illustrating a) synthesis of triethoxysilanes from MPTES/alkenes and b) synthesis of trimethoxy- and triethoxysilanes from APTES/thiols or MPTMS/alkenes.

FIG. 19 shows schematic of the chemical reactants and associated conditions for and data from thiol-ene reactions catalyzed using Norish type I/II photoinitiators (molecules A and B), a thermal initiator (C), or triethylborane/oxygen (D). UV light sources for all photoinitiated reactions were carried out with a 15 W blacklight ($\lambda$max=368 nm). Triethylborane reactions were setup under backfilled argon flasks and then exposed to air for 5 min to initiate reactions.

DETAILED DESCRIPTION OF THE INVENTION

Figure 1:
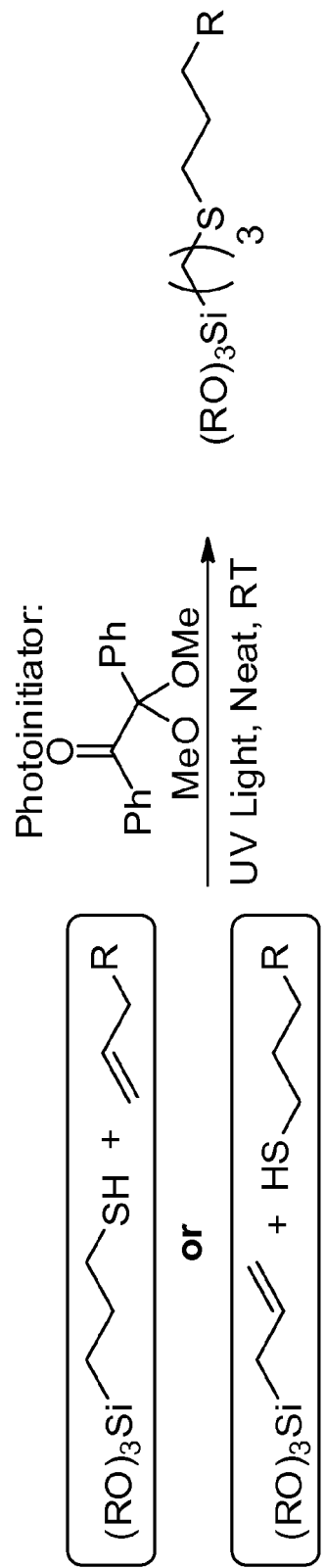
FIG. 1 is a schematic illustrating a general methodology of the present invention for synthesis of trialkoxysilanes using a photoinitiator.

Unless otherwise defined, all terms of art, notations and other scientific terms or terminology used herein are intended to have the meanings commonly understood by those of skill in the art to which this invention pertains. Many of the techniques and procedures described or referenced herein are well understood and commonly employed using conventional methodology by those skilled in the art. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

As is known in the art, a highly desirable feature of silane compounds is their reactivity, i.e. that they are easily grafted onto many types of surfaces, including silica and metal oxides. For this reason, one of the simplest routes to modifying the physicochemical properties of many surfaces is to functionalize them using trialkoxysilanes containing pendant functional groups (see, e.g., Luo, S., et al. *Adv. Synth. Catal.*, 2007, 349, 2431-2434; Kim, O. H., et al. *ACS Nano*, 2010, 4, 3397-3405; Baldacchini, T., et al. *ACS Nano*, 2006, 22, 4917-4919). Embodiments of the invention disclosed herein harness these properties of silanes, for example, in methodologies designed to modify and control, for example, the physical and chemical properties and reactivity of planar and particular solid interfaces, fabricating sensors and chemical devices, and synthesizing inorganic-organic hybrid materials.

As discussed in detail below, embodiments of the present invention can be used to produce a huge variety of functionalized silane compounds through the use of radical-based thiol-ene or thiol-yne chemistry to form sulfide linkages between molecules containing free thiols (—C—S—H) and molecules containing, for example unsaturated carbon atoms as occurs on alkenes and alkynes ("alkenes/alkenes"). Embodiments of the present invention that include methods involving the addition of one thiol across an alkene or two thiols across an alkyne, are members of the class of modular "click" reactions (see, e.g., Kolb, H. C., et al. *Angew. Chem., Int. Ed. Engl.* 2001, 40, 2004). In embodiments of the invention, these thiol-ene/thiol-yne reactions can proceed under mild conditions in the presence of oxygen (e.g., oxygen tolerant). Such reactions are regioselective, tolerate many functional groups, and can be run neat or in benign solvents such as water. In view of this, embodiments of methods disclosed herein allow the synthesis of trialkoxysilanes with nearly any desired pendant functionality. In addition, embodiments of the invention provide quantitative or near-quantitative yields with simple or no purification required. With these attributes, the present invention is well suited for synthesizing functionalized trialkoxysilanes for a variety of applications, such as surface coating applications that are designed to modify the material property of that surface.

Figure 5:
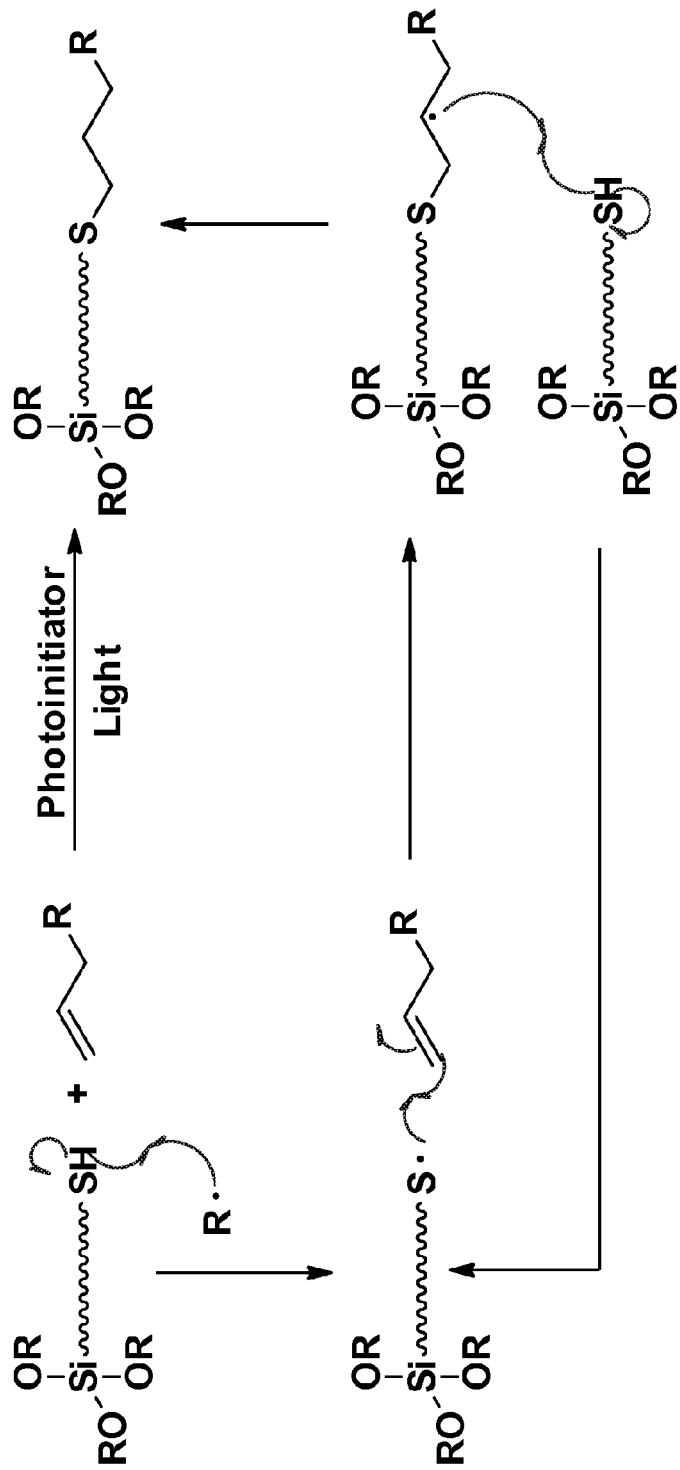
FIG. 5 is a schematic illustrating one embodiment of the thiol-ene reaction mechanism for the synthesis of functional trialkoxysilanes.
Figure 6:
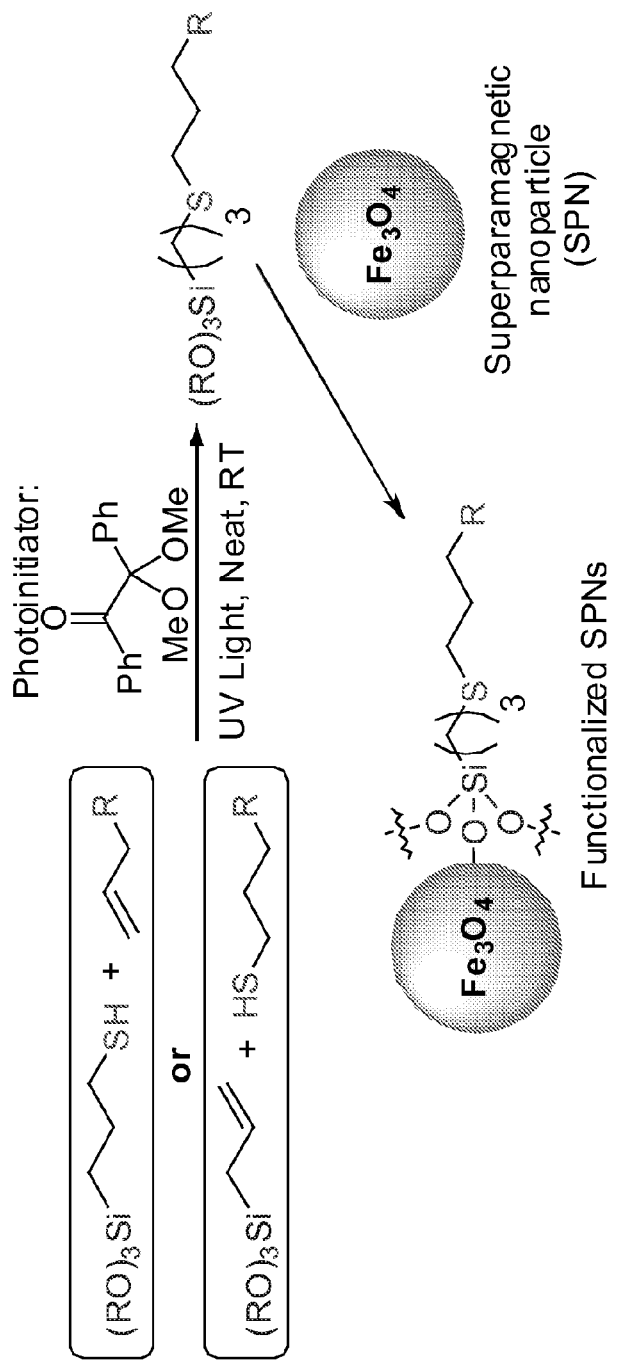
FIG. 6 is a schematic illustrating another embodiment of the thiol-ene reaction mechanism for the synthesis of functional magnetite SPNs.

Aspects of reaction mechanisms useful in embodiments of the invention, kinetics, and applications of the thiol-ene reaction have been previously studied (see, e.g., Dondoni, A. *Angew. Chem. Int. Ed.* 2008, 47, 8995-8997; Hoyle, C. E., et al. *Angew. Chem. Int. Ed.* 2010, 49, 1540-1573; Kade, M. J., et al. *Polym. Sci., Part A: Poly. Chem.* 2010, 48, 743-750; Hoogenboom R. *Angew. Chem. Int. Ed.* 2010, 49, 3415-3417). Briefly, without being bound by a specific theory or mechanism of action, it appears that the general reaction between a free thiol moiety ("—S—H") and alkene/alkyne, initiated by a radical initiator, proceeds in the manner shown in FIGS. 5 and 17. In this reaction, the radical initiator abstracts a labile hydrogen atom from a thiol molecule to form a thiyl radical. The thiyl radical then attacks the alkene/alkyne to form the regioisomeric radical intermediate, typically with the radical at the most substituted carbon or in the most stable position. This intermediate then undergoes chain transfer by abstracting another hydrogen atom from a second thiol group (on the same or a different molecule), to form a complete thioether linkage and a new thiyl radical. The newly formed thiyl radical then reacts with another molecule of alkene/alkyne. This process repeats until one or more (e.g. all) of the reactants are consumed (e.g. the thiol and/or alkene/alkyne compounds). In this process, the resulting thioether bonds provide a strong covalent linkage, for example a linkage between a silane moiety on one portion of the molecule that can couple the compound to a surface and a pendant functional group on another portion of the molecule that can provides a desired material property and/or functionality. The modular mechanism of action of the specific chemical synthesis processes disclosed herein, one where the intermolecular and/or intramolecular atomic reactions are driven by the discrete trialkoxysilane moieties on compounds, in combination with the discrete sulfhydryl moieties on compounds, in combination with the discrete unsaturated carbon moieties on alkene and alkyne compounds (in combination with a radical initiator) allows artisans to utilize an enormous number of different compounds selected to have specific functional groups in various embodiments of the invention.

Precedents for this approach include several syntheses of small quantities of individual functional trimethoxysilanes for specific applications (see, e.g., Tong, B. H., et al. *J. Photochem. Photobiol., A* 2007, 191, 74-79; Shiels, R. A., et al. *J. Mol. Catal. A: Chem.* 2007, 261, 160-166; Tong, B. H., et al. *Photochem. Photobiol. Sci.* 2007, 6, 519-520), and the preparation of silicones and polymer-silane conjugates (see, e.g., Grande, J. B., et al. *Dalton Trans.* 2010, 39, 9369-9378; Campos, L. M.; Killops, K. L., et al. *Macromolecules* 2008, 41, 7063-7070; Sengupta, S. S., et al. *Polym. Eng. Sci.* 2006, 46, 480-485; Parent, J. S., et al. *Macromolecules* 2005, 38, 5538-5544; Youssef, B., et al. *Nucl Instrum Meth B* 1999, 151, 313-317). Radical-based thiol-ene reactions have been widely used to synthesize dendrimers (see, e.g., Rissing, C., et al. *Organometallics* 2009, 28, 3167-3172; Killops, K. L., et al. *J. Am. Chem. Soc.* 2008, 130, 5062; Lorenz, K., et al. *Macromolecules* 1997, 30, 6860-6868), to functionalize biomolecules, biomacromolecules and surfaces, and to synthesize new polymeric materials for applications ranging from soft lithography to porous microparticles (see, e.g., Dondoni, A. *Angew. Chem., Int. Ed. Engl.* 2008, 47, 8995-8997; Franc, G., et al. *Chem. Soc. Rev.* 2010, 39, 1536-1544; Hoyle, C. E., et al. *Angew. Chem., Int. Ed. Engl.* 2010, 49, 1540-1573; Kade, M. J., et al. *J. Polym. Sci., Part A*: Polym. Chem. 2010, 48, 743-750). However, the conventional art teaches that such techniques require an excess of one or more reactants and/or or a large excess of solvent. Moreover, the art does not teach that these methodologies are applicable to a wide range of chemical functional groups under mild conditions with different radical initiators. In addition, such known processes do not focus on techniques selected to optimize product purity, for example in the case of the small molecular silanes. For these reasons, such conventional methods are problematical for artisans wishing to, for example, employ chemical synthesis methodologies that are environmentally friendly and not require the use of and/or produce a large amount of hazardous materials (e.g., solvents in which the reactants are disposed, reaction byproducts, chemicals used to extract or otherwise purify desired compounds from a reaction mixture, etc.). In addition, these conventional methods are problematical for artisans wishing to employ simple and inexpensive methods for producing trialkoxysilane compounds in a relatively purified form.

As discussed below, a significant advantage of embodiments of the present invention is that the methods disclosed herein can be used to form trialkoxysilanes products in a high yield that enables their immediate use of the product without further purification. In embodiments of the invention, crude products are formed in quantitative or near-quantitative yields and in high purity (e.g., a purity generally greater or equal to 94% and an average purity around 96%). Interestingly, this degree of purity is equivalent to, or greater than, the purity of many commercially available silanes. Because the synthesized materials can be made using methodologies designed to produce compounds having a very high purity, for many applications, these compounds do not have to undergo further purification steps following the initiation of the reaction, for example, further steps involving the distillation, crystallization, extraction, chromatographic separation of the reaction product. Embodiments of the silane synthesis process can be designed to run neat (i.e., without solvent), and in this way produce little or no waste. In addition, the reactions also proceed under mild reaction conditions in the presence of oxygen and benign solvents, thereby making them more environmentally friendly as compared to conventional methodologies.

As noted above, embodiments of the invention have a number of advantageous properties that allow them to solve certain problems observed in conventional synthesis reactions. For example, embodiments of the invention can use exact stoichiometric amounts of thiol and alkene (or 2:1 thiol to alkyne) in order to, for example, control the purity of the end product. Embodiments of the invention utilize reactions that can also be run neat, which reduces the need for environmentally unfriendly solvents. Moreover, in embodiments that use a solvent to dissolve reactants, only a minimal amount is typically required. Embodiments of the invention can include less than 1%, 2%, 3%, 4%, 5%, 6%, 7%, 8%, 9%, 10%, 20%, 30%, 40%, 50%, 60% or 70 wt % solvent. Similarly, only minimal catalytic amounts of radical initiators are used in the reaction. Any volatile non-interfering byproducts that result from an embodiment of the invention can be easily removed by vacuum after reaction completion. Embodiments of the invention have further advantageous properties in view of the observation that the disclosed reactions are very functional group tolerant. In one illustration of this, the working examples below show exemplary reactions with both small and large complex molecules. Moreover, embodiments of the invention can be used with a number notable molecular motifs that which are particularly important and have not been shown to work with conventional thiol-ene protocols include, for example, unprotected carboxylic acids, fluorophores, complex acid- and base-sensitive protection groups, highly charged guanidinum groups, and amino acids. In addition, photoinitiation reactions can typically be run in standard borosilicate glass with inexpensive low power 15 W blacklight(s) (two lamps were used when doing scaled up reactions of >30 g) and on average reach >94% conversion, a low power yet efficient embodiment.

The invention disclosed herein has a number of embodiments. One illustrative embodiment is a method for making a trialkoxysilane compound comprising a thioether by forming a mixture comprising a trialkoxysilane compound, a compound comprising a sulfhydryl moiety, an alkene compound or an alkyne compound, and a radical initiator agent. Another illustrative embodiment is a method for making a trialkoxysilane compound comprising a thioether by forming a mixture comprising a trialkoxysilane compound, a compound comprising a disulfide moiety, an alkene compound or an alkyne compound, and a radical initiator agent. In such embodiments, the mixture is then subjected to conditions that initiate a chemical reaction in the mixture so that the trialkoxysilane compound comprising the thioether is made. Typically these conditions involve modulating the activity of the radical initiator agent by exposing the mixture to light, heat or oxygen. In an illustrative embodiment of the invention, the radical initiator agent is modulated by exposure to light, a condition that allows it to react with a hydrogen atom in a first sulfhydryl moiety so as to form a thiyl radical. In this embodiment, the thiyl radical reacts with the alkene or the alkyne so as to form a radical intermediate; and the radical intermediate then reacts with a hydrogen atom in a second thiol moiety so as to form a thioether bond between the sulfur atom of the sulfhydryl moiety and an unsaturated carbon atom in the alkene or alkyne, with a consequence of this reaction being the formation of the trialkoxysilane compound comprising the thioether. Typically, this carbon atom that is covalently linked to the sulfur atom is a terminal carbon atom or a strained carbon atom in the alkenes/alkynes.

As noted above, embodiments of the invention use trialkoxysilane compounds as starting reagents. The structure of trialkoxysilane moieties used in embodiments of the invention (i.e. to allow grafting to surfaces) is well known in the art and shown for example in various Figures. The "alkyl" groups of these compounds typically includes linear and/or branched hydrocarbon structures and combination thereof, which may be fully saturated, mono- or polyunsaturated. A review of the various trialkoxysilane compounds disclosed herein to illustrate the versatility of these molecules shows that such compounds can have a number of different architectures and include a variety of other atoms and/or groups such as sulfhydryl groups, terminal alkenes and the like.

As illustrated for example by a review of the many trialkoxysilane compounds that are commercially available from companies such as SIGMA-ALDRICH AND GELEST INC., typical starting silane materials are widely available, inexpensive and can, for example be purchased ready-made with groups such as a free thiols or terminal alkenes. This allows one to easily modify the pendant group with a thiol, alkene, or alkyne. The wide availability of and flexible design parameters of trialkoxysilane compounds helps circumvent tedious protection and deprotection steps when synthesizing a desired pendant group. In addition, relatively reactive trimethoxysilane starting materials readily work with embodiments of the invention disclosed herein. In embodiments of the invention, the components of the reaction mixtures and/or the reaction conditions are controlled so as to control the characteristics of the product produced by such processes.

As noted above, the modular and specific natures of the moieties involved in the "click" reactions disclosed herein allows a high degree of molecular flexibility when forming reaction mixtures to use with embodiments of the invention. As shown in FIG. 1, in certain embodiments of the invention, the trialkoxysilane compound added to the mixture comprises the sulfhydryl moiety. As also shown in FIG. 1, alternatively the sulfhydryl moiety is on a different compound. As also shown in FIG. 1, in certain embodiments of the invention, the trialkoxysilane compound added to the mixture comprises the unsaturated carbon (alkene/alkyne). As also shown in FIG. 1, alternatively the unsaturated carbon (alkene/alkyne) is on a different compound. As shown in FIG. 3, in certain embodiments of the invention, the compound that comprises an unsaturated carbon atom (alkene/alkyne) also comprises a sulfhydryl group. As shown in FIG. 2, in certain embodiments of the invention, the compound that forms a thioether linkage with a trialkoxysilane group comprises a functional group (e.g., glucose) or groups as well as an unsaturated carbon atom (alkene/alkyne).

In certain embodiments of the invention, the method comprises mixing a trialkoxysilane precursor containing single or multiple alkenes with a molecule containing one or multiple thiols so that the molar equivalents of alkene and thiol groups are 1:1. In other embodiments of the invention, the method comprises mixing a trialkoxysilane precursor containing single or multiple alkynes with a molecule containing one or multiple thiols so that the molar equivalents alkyne to thiol is 1:2. In still further embodiments of the invention, the method comprises mixing a trialkoxysilane precursor containing one or more free thiol groups with another molecule containing an equivalent or unequivalent amount of alkenes or alkynes, for example, molar ratios of 1:1 for thiol to alkenes and 2:1 for thiol to alkynes. Typically, the mixture does not comprise a metallic catalyst agent or a chiral organic ligand. Optionally, the reaction is performed in the presence of an inert gas such as $N_2$.

In some embodiments of the invention, the mixture comprises less than 40, 35, 30, 25, 20, 15 or 10 weight percent of a solvent. In some embodiments of the invention, the mixture comprises less than 5 weight percent of a solvent. In certain embodiments of the invention, the mixture does not comprise a solvent. In embodiments of the invention, the reaction mixture is typically homogenized. In embodiments of the invention, minimal amounts of anhydrous or nearly anhydrous organic solvents may be added. For example, if one or more of the reaction components are not fully dissolved, a minimal amount of an anhydrous or nearly anhydrous organic solvent may be added to facilitate in dissolving all of the components and homogenizing the mixture. The mixture may also be briefly purged with an inert gas. Following the reaction, certain embodiments of the invention can further comprise placing the composition of matter under a negative pressure to remove a constituent of the composition of matter having a vapor pressure higher than the trialkoxysilane compound comprising the thioether (e.g., a solvent, a radical initiator etc.).

In some embodiments of the invention, the components of the reaction mixture and/or the reaction conditions are controlled so as to control the purity of the thioether product produced by such processes. For example, in some embodiments of the invention, the components of the reaction mixture and/or the reaction conditions are controlled so as the reaction produces a composition of matter wherein the trialkoxysilane compound comprising the thioether has a high degree of purity, for example a composition where this compound is at least 80%, 85%, 90% or ≥95% pure. In the working embodiments of the invention discussed below, the crude products are usually >90% pure with the majority being >94% pure, and consequently do not have to be purified chromatographically or by filtration or crystallization. Some working embodiments have >99% conversion with crude products being 97% pure. As compared to prior art processes, such embodiments of the invention reduce costs, time, and waste.

In some embodiments, the chemical reaction is performed as a one-pot synthesis. As is known in the art, a "one-pot synthesis" is a strategy to improve the efficiency of a chemical reaction whereby a reactant is subjected to successive chemical reactions in just one reactor. This is much desired by artisans in this technology because avoiding a lengthy separation process and purification of the intermediate chemical compounds saves time and resources while increasing final chemical yield. In certain embodiments of the invention, the chemical reaction in the mixture produces a yield of at least 75%, 80%, 85% or 90% or ≥95% of the trialkoxysilane compound comprising the thioether linkage.

Another embodiment of the invention is method for modifying a surface of a material by using a compound generated by a process disclosed herein to couple one or more functional groups to that surface/material. In such methods, the silane groups on the compounds are relied upon for their ability to be easily grafted onto many types of surfaces, the functional group are relied upon for their ability to modify the surface of the material and the processes disclosed herein are relied upon to join the silane group and the functional group together via thioether bonds, bonds which are known to provide a strong covalent linkage. Embodiments of the invention include a first step of making a trialkoxysilane compound comprising a thioether by forming a mixture comprising a trialkoxysilane compound, a compound comprising a sulfhydryl moiety, an alkene compound or an alkyne compound, and a radical initiator agent. In this method, the mixture is then subjected to conditions that initiate a chemical reaction in the mixture so that the trialkoxysilane compound comprising the thioether is made. Following this synthesis of the trialkoxysilane compound comprising the thioether, this compound is then covalently coupled to the surface of a material so that the surface of the material is modified. In an illustrated embodiment of the invention, the surface is hydroxylated and the trialkoxysilane compound comprising the thioether is covalently coupled to the surface via an oxane bond. Optionally, the trialkoxysilane compound comprising the thioether is coupled to the surface of the substrate in the absence of any distillation or chromatography purification steps following its formation in the reaction mixture.

Optionally in such embodiments of the invention, the alkene, the alkyne or the compound comprising a sulfhydryl moiety is covalently linked to a pendant group comprising one or more functional groups such as an imaging agent, a surface wetting agent, a water repelling agent, an antimicrobial agent, a therapeutic agent, a ligand or a catalytic agent, so that the surface is modified by having the functional group coupled thereto. In illustrative embodiments of the invention, the surface to which the compound is coupled comprises a silicon oxide composition, a metal composition, a plastic composition a silicone composition or a plastic composition and, for example, is part of a nanoparticle, a membrane, a chromatographic matrix, a biological or chemical sensor, a microfluidic device, a silicon chip, a micro-electrical mechanical device, an optical material or a light emitting device. Embodiments of the invention further include a material, a matrix, a particle, or a device having a surface modified according to the methods disclosed herein.

As discussed below, the methods disclosed herein allow the synthesis of trialkoxysilanes with nearly any specific pendant functionality. In this context, another advantage of embodiments of the present invention is that almost any small molecule or macromolecule can therefore be easily coupled to a trialkoxysilane. Therefore, the modular aspects of the present invention fill such a need by providing enormous flexibility in synthesizing tailored, functional trialkoxysilanes that meet the demands of many applications, current and future. While trialkoxysilanes are widely used to create or functionalize superhydrophobic surfaces, organic photovoltaics, magnetic and mesoporous metal oxides, and sensors, currently there are relatively few methods for synthesizing functional trialkoxysilanes. Significantly, the thiol-ene/thiol-yne reactions disclosed herein are regioselective and functional group tolerant. Illustrative uses of silanes synthesized by embodiments of the present invention include: preparation and/or production of adhesives, sealants, advanced ceramics, battery materials, heterogeneous catalysts, conductive coatings, cosmetic materials, polymer composites, and dielectric, hydrophilic, superhydrophobic, and photovoltaic materials. These silanes can also be used in the construction of nanoparticles, membranes, chromatographic supports for chemical separations (see, e.g. Wang et al., Talanta (2012), 91, 52-59, the contents of which are incorporated by reference), chemical and biological sampling systems, microfluidic platforms, microelectromechanical devices and systems, and lab-on-a-chip devices, biological and chemical sensor and diagnostic devices, and nano- and microarrays. A substantial application for the present innovation is the production of trialkoxysilanes with small biomolecules such as pendant groups. These silanes can, for example, be used in the creation of biomedical diagnostic devices, drug delivery vehicles, and improved MRI contrast agents.

The observations that the disclosed modular addition or "click" reactions are very functional group tolerant allows a large number of agents or functional groups to be coupled to silanes in embodiments of the invention, for example in order to allow their immobilization to a surface. For example in certain embodiments of the invention, the disclosed modular addition or "click" reactions are used in the preparation of surface immobilized catalysts, for example, those used in recyclable heterogeneous catalysis. In embodiments of the invention, functional groups comprising molecules, macromolecules, biomolecules, and biochemicals can be immobilized on the surfaces of any metal oxides, oxidized polymers, mesoporous supports, and any macro, micro or nanoparticles with a full or partially oxidized surface. One illustrative surface/support that is particularly important in this technical field is magnetic nanoparticles (e.g., due to the ease of magnetic separation from suspensions).

Embodiments of the invention utilize functional groups comprising organic catalysts or ligands that are capable of directing and performing a wide variety of functions such as polymerization, oxidation, reduction, alkylation, rearrangements, cross-coupling, substitution, electron transfer, elimination reactions and the like. In embodiments of the invention, such catalysts and/or ligands can direct reactions with chemo, regio, and/or steroselectivity and/or specificity. In embodiments of the invention, illustrative functional groups that can be coupled to silanes include 2,2,4,4,-tetramethylpiperidinyl-1-xyl, 2-iodoxybenzoic acid, amino acids such as L-proline, McMillans catalyst, N,N-dimethylaminopyridine, trialkylphosphines, chiral boranates as well as engineered peptides, polypeptides, enzymes (e.g., trypsin) and the like. Embodiments of the invention can include functional groups comprising organometallic catalysts or ligands capable of directing and performing polymerization, oxidation, reduction, alkylation, rearrangements, cross-coupling, substitution, electron transfer or elimination reactions. In embodiments of the invention, such catalysts and/or ligands can direct reactions with chemo, regio, and/or steroselectivity and/or specificity. In embodiments of the invention, illustrative functional groups that can be coupled to silanes include Grubbs ruthenium metathesis catalysts, Copper(I)-L-proline (e.g., for Ullmann reactions), Palladium(II) and platinum(II) acetates (e.g., for cross-coupling reactions such as Sonogishira reactions), $Ru(bpy)_3^{+2}$ for electron single electron transfer reactions, Iron-Heme complexes and the like.

Embodiments of the invention can also include functional groups useful, for example in chromatographic separation techniques. Using embodiments of the invention, various functional groups comprising desirable molecular structures may be immobilized on chromatographic packing materials such as silica gel, sol-gel monoliths, poly(dimethylsiloxanes), porous silica, or membranes (these are just a few specific examples) to create surfaces with different polarity, charge, chirality, wettability, or micro/nanostructures which can effect separation of complex mixtures of molecules, macromolecules, biomolceules, or inorganic species. One illustrative example of the use of silanes as disclosed herein is in functionalizing the surface of silica gel with a chiral amino acid or quinolines and then using this silica to pack a column to do separation of enantiomeric or diasteromeric mixtures. Such approaches are used to make columns for high pressure liquid chromatography, and gas chromatography/mass spectrometry. In addition, using embodiments of the invention, one can modify the polarity and wettability of a packed column by changing the surface functionalization to say a long chain alkane like tetradecane, or one can alternatively make the column charged for separation of anions and cations by immobilizing quaternary ammonium or phosphonium groups (e.g., tetramethylammonium chloride or triphenylmethylphosphinum chloride). Embodiments of the invention can also be applied to separate molecular species using a membrane.

Embodiments of the invention can also include functional groups useful, for example, in the modification of surface wettability, adhesion, and tribological properties. For example, in certain embodiments of the invention, wettability can be changed by immobilizing nonpolar molecules like dodecane, or perfluoroispropane to change the macroscopic contact angle of liquids. The same approach also often leads to changes in the tribological properties of surfaces. Modifying surfaces having nano to micro roughness with fluorinated groups can result in the creation of superhydrophobic surfaces which are extremely water repellent and are of great interest for developing self-cleaning materials. Using embodiments of the invention, the adhesion and tribological properties of surfaces can also be changed by immobilizing silanes with short polydimethylsiloxane pendant groups that are used to decrease friction between different surfaces. Immobilizing silanes containing pendants such as perfluorophenylazides (PTFP) can also be used to change the adhesion between surfaces. As is known in the art, PTFP forms reactive nitrenes when irradiated with deep UV light which can insert into bonds on an adjacent surface to change the overall surface adhesion.

Surfaces modified using embodiments of the invention disclosed herein can be found in a wide variety of materials and devices. For example, specific molecules or macromolecules (e.g., polypeptides such as antibodies and/or polynucleotides such as primers and probes) can be immobilized to surfaces to create sensors. In illustrative embodiments, these molecules can provide elements that cause or transduce a measureable signal when exposed to a specific analyte or analytes, or an element that makes a more complex device function. An illustrative functionality is modifying surface wettability, for example to prevent nonspecific adsorption of contaminants, such as in protein biomarker detection, or to act as the transducer for the measureable signal. An example of a transducer can be found in electrochemical sensors where small conjugated p-phenylene vinylenes are used as antenna on conducting surfaces for transferring electrons to the underlying conducting surface. Illustrative devices include chemical and biological sensors for portable diagnostic medical devices, for example sensors for chemical or biological warfare agents as well as sensors for chemical or biological markers used to diagnose and treat medical disorders and diseases. Sensors can further utilize micro/nanoparticles. For example immobilization of a guanidinum silane to silicon nanoparticles results in a potent DNA sensor. The guanidinum binds tightly to negatively charged DNA which results in a change of the silicon quantum dots fluorescence.

Embodiments of the invention can also include functional groups useful, for example, in the modification of surfaces used in energy harvesting devices and materials. Because embodiments of the disclosed synthetic methodology have thermal, photo, and oxygen initiation methods, these processes allow the formation of silanes with photosensitive pendant groups. In such embodiments, the types of silanes that can be immobilized are those that enhance or themselves are capable of absorbing photons and storing or using their energy. These silanes can be deposited on conducting surface such as indium-tin-oxide, gold, and cadmium selenide. Specific categories of devices under this heading include: photovoltaics, organic and inorganic solar cells, light emitting diodes, thin-film transistors, water splitting devices. Examples of this molecules immobilized to make these devices function are organometallic complexes containing ruthenium and aromatic ligands such as $Ru(Byp)_3^{+2}$. Other examples of purely organic materials used to make these devices function are p-phenylene vinylene and porphorins, which can be immobilized.

Embodiments of the invention can also include functional groups useful, for example, in the modification of surfaces used in drug delivery vehicles, micro/nanoparticle probes and the like. In certain embodiments of the invention, caged (e.g., silenced drugs also known as prodrugs) drugs and imaging agents can be immobilized to carriers for drug delivery and to probe biological environments (e.g., environments such as those inside and surrounding cells). Examples of materials that can be immobilized for drug delivery using embodiments of the invention include caged taxol, ferroquine or cisplatin. An example of a class of imaging materials that can be immobilized is organometallic europium complexes. In embodiments of the invention, silane compound embodiments of the present invention can be used to mask nanoparticles that act as the imaging agent such as magnetite. In this case, the silane coating, such as those having oligo ethyleneglycol pendant groups, can be used, for example, to improve the pharmacokinetics of an imaging agent.

In certain embodiments of the present invention, methods are provided for producing chemically tailored trialkoxysilanes used in the fabrication of a host of useful materials and devices, including catalyst-coated nanoparticles (e.g., magnetic Mortia-Baylis-Hillman catalyst), superhydrophobic surfaces (e.g., utilizing a fluorosilane), chemosensors, and LEDs (e.g., utilizing phosphorescent-silane). Such embodiments of the invention can be used to alter the physicochemical properties of the surface of a matrix and/or substrate, including for example, properties such as surface wettability by liquids, tribological properties, optical and electrical properties, redox activity, and the propensity of chemical or biological substances to adsorb, adhere and chemically bond to a surface.

Embodiments of the present invention include methods for the preparation of diverse, inorganic and inorganic/hybrid materials, including polymer composites. Certain embodiments include, but are not limited to, chromatographic supports for chemical separations, membranes, heterogeneous catalysts, and micro- and nanoparticulate labels and probes. Other exemplary implementations include the fabrication of chemical, analytical and MEMs-type devices, including chemical and biochemical sensors and arrays, portable medical diagnostics, photovoltaics, optical components and light-emitting diodes (LEDs).

As noted above, embodiments of the invention include processes for synthesizing functional silanes, for example a trialkoxysilane with a pendant/functional group having a selected property or characteristic, utilizing the radical-based thiol-ene or thiol-yne chemistry disclosed herein. Illustrative embodiments include methods that comprise the steps of mixing a trialoxysilane precursor containing an alkene or alkyne with a molecule containing a thiol, adding a radical initiator to the mixture, and exciting the radical initiator in the mixture. FIGS. 1, 5, 16, 17, 21 and 22 illustrate general approaches on how a thiol-ene reaction is used to produce trialkoxysilanes with any type of pendant group or functionality, denoted R. In some embodiments, the pendant group is linked through a thioether bond to the trialkoxysilane group. The tethered pendant/functional group may be a hydrophilic polymer, a hydrophobic polymer, a small molecule, synthetic macromolecule, biomolecule or biopolymer. Illustrative embodiments include methods that comprise the steps of mixing a trialoxysilane precursor containing a thiol with a molecule containing an alkene or alkyne, adding a radical initiator to the mixture, and activating the radical initiator in the mixture. It is also contemplated that a molecule containing multiple thiol and/or alkenes/alkynes may be used in embodiments of the invention.

In illustrative embodiments of the invention, silanes can be synthesized in the absence of solvent with low flux, and low power electromagnetic radiation. In such embodiments, silane production can be easily scaled up while maintaining quantitative product conversion and high product yield or purity. In illustrative embodiments of the invention, small and large-scale synthesis can be achieved, for example using standard borosilicate glass reactors and low flux UV light. These features greatly reduce the power and material costs of making the desired compounds as compared with conventional methods. Additionally, many of the starting materials (thiols and alkenes) used in embodiments of the invention are either commercially available, or can be synthesized in one to two steps from commercial materials and then converted into silanes. For this reason, embodiments of the invention can be readily scaled to yield desirable product on the gram-scale in the laboratory, for example for artisans requiring designer molecules adapted for a specific application. Alternatively, process embodiments of the invention can be scaled-up for larger preparatory or commercial production.

Embodiments of the radical-based thiol-ene reaction described herein involve the stoichiometric addition of one thiol across one or an alkene or the stoichiometric addition of two thiols across one alkyne. The reaction may also take place between multiple thiol and alkene and/or alkynes on a single molecule, macromolecule, or biomolecule. Continuous generation of small amounts of reactive radicals is all that is required to initiate and propagate the reaction, which is typically run neat. Initiation of such radical-based thiol-ene reactions can be achieved by using catalytic amounts radical initiators. Typically, radical initiators are substances that can produce radical species under mild conditions and promote radical reactions. These substances generally possess bonds having small dissociation energies. Illustrative radical initiators for use in embodiments of the invention include photoinitiators such as Norish type I initiators. Illustrative initiators include benzoin ethers, benzils, α-hydroxyl, or α-alkoxy, or α-aminoalkylphenones, and acylphosphine oxides. Specific examples include benzoin ethyl ether, benzoin isobutyl ether, benzoin, benzil, 2,2-diethoxyacetophenone, 4'-hydroxyacetophenone, 2-Benzyl-2-(dimethylamino)-4'-morpholinobutyrophenone, and diphenyl(2,4,6trimethyl-benzoyl)phosphine oxide. Illustrative radical initiators for use in embodiments of the invention also include Northis type II initiators. Examples include thioxanthones and benzophenones. Specific examples include thioxanthen-9-one, 2-chlorothioxanthen-9-one, 4-(dimethylamino)benzophenone, and 4,4'-dihydroxybenzophenone. Illustrative radical initiators for use in embodiments of the invention also include Northis Metal-ligand electron transfer initiators such as (cumene) cyclopentadienyliron(II) hexafluorophosphate, ferrocene, and tris(2,2'-bipyridyl)dichlororuthenium(II) hexahydrate. Other common photoinitiators and sensitizers capable of initiating reactions in embodiments of the invention include photoacid generators such as triarylsulfonium hexafluorophosphate and diphenyliodonium nitrate (which can be used to carry out the thiol-ene and also induce surface coatings of these silanes). In addition, absorbing triplet sensitizers with triethylamine can also be used, for example thioxanthen-9-one with triethylamine and curcumin with tris(2,2'-bipyridyl) dichlororuthenium(II) hexahydrate.

Illustrative radical initiators for use in embodiments of the invention include thermal initiators. For example, the Vazo® initiators or any diazoinitiators will work with certain embodiments of the thiol-ene reaction. In typical embodiments of the invention the initiation temperatures range from ~40-100° C. Specific examples of typical initiators include 2,2'-azobisisobutyronitrile (AIBN), 4,4-azobis(4-cyanovaleric acid), and 1,1'-azobis(cyclohexanecarbonitrile). In addition, organic peroxides and organic nitrites have high initiation temperatures and can be useful in embodiments where one wants to melt a solid reactant and run the thiol-ene reaction neat. Specific examples of these initiators include benzoyl peroxide, tert-butyl peroxide, lauroyl peroxide, dicumyl peroxide and tert-butylnitrite. Illustrative radical initiators for use in embodiments of the invention further include oxygen reactive initiators. In certain embodiments of the invention, the initiator is a trialkylborane. These initiators are pyrophoric and air sensitive. Upon exposure to air they react very rapidly to produce alkyl radicals which can abstract hydrogen atoms from thiols to initiate the thiol-ene reaction (See discussion and tables noted in Example 10 below). Examples of borane initiators include tritheylborane, triphenylborane and diethylmethoxyborane.

Illustrative embodiments of the invention comprise the steps of adding a catalytic amount of a radical initiator as disclosed herein to the reactant mixture and exciting the radical initiator in the mixture to form free radicals and drive the reaction. The thiol-ene/thiol-yne reaction cycle disclosed herein is catalyzed by small amounts radicals generated for example from a radical initiator. Initiating radicals rapidly abstract hydrogen atoms from thiols which sets off a catalytic cycle of radical additions to alkenes followed by chain transfer reactions (see, e.g., FIG. 5, FIG. 17, and FIG. 21). While 3-mercaptopropyltrialkoxysilane is depicted as the silane precursor in FIG. 1, it can be replaced with any other silane precursor, such as allyltrialkoxysilane, which can react with thiol/sulfhydryl containing molecules.

Typical illustrative embodiments of the invention utilize a radical photoinitiator. In exemplary implementations, the reaction mixture is placed in an optically transparent container that allows externally applied radiation to excite the photoinitiator. The reaction mixture is irradiated using low power UV or visible light to initiate free radical formation and drive the reaction. Reactions are run neat (e.g., absent any additional solvent) or in the presence of a minimal amount of solvent (0.2-1 mL) in standard borosilicate glass reactor. In certain exemplary implementations, the reactions are run long enough to ensure complete reaction (for example, more than 97% reacted) of all the reactants. No further product purification is required for most applications, although this can be done by existing methods if necessary. If solvent was used, it may be removed under vacuum. If the radical initiator or its degradation derivatives are volatile, they can also be removed under vacuum. In one exemplary implementation, the method comprises mixing equivalent amounts of a 3-mercaptopropyltrialkoxysilane and an allyl/terminal alkene, or of a thiol and allyltrialkoxysilane, in the presence of a 2 mol % photoinitiator. In one exemplary implementation, the method comprises mixing equivalent amounts of a 3-mercaptopropyltrialkoxysilane (MPTES) and an allyl/terminal alkene, equivalent amounts of a 3-mercaptopropyltrimethoxysilnae (MPTMS) and an allyl/terminal alkene, or of a thiol and allyltrialkoxysilane (ATES), in the presence of a 2 mol % photoinitiator. The mixture is irradiated at room temperature, typically for approximately 24 hours, under an argon or nitrogen blanket using a low power 15-W blacklight ($\lambda_{max}$=368 nm with a total UV output of 2.2 W).

In other embodiments of the invention, the method comprises adding a catalytic amount of a thermal radical initiator or thermal initiator. The mixture should be homogenized and if one component does not fully dissolve, then a minimal amount of an anhydrous organic solvent may be added to fully dissolve all of the components and homogenize the mixture. The mixture may also be briefly purged with an inert gas. Unlike exemplary implementations which use a photoinitiator, when a thermal initiator is used the reaction vessel does not need to be transparent. The reaction mixture is heated to the appropriate temperature to create free radicals and drive the reaction. Reactions are run neat or in the presence of a minimal amount of solvent (0.2-1 mL). In certain exemplary implementations, when the reactant conversion reaches greater than 97%, the reaction is deemed complete. Typically, product yields are greater than 96%. The reactions may be monitored, for example, by proton nuclear magnetic resonance spectroscopy. No further product purification is required for most applications, although this can be done by existing methods if necessary. If solvent was used, it may be removed under vacuum. If the radical initiator or its degradation derivatives are volatile, they can also be removed under vacuum.

Embodiments of the methods are disclosed herein utilize thiol-ene/thiol-yne reactions in a simple and efficient way to synthesize functional triethoxy and trimethoxysilane surface coating agents. In certain embodiments, the methodology uses inexpensive MPTES, MPTMS, or ATES silane precursors, alkenes or silanes that are commercially available or easily prepared in one to two steps, a low mol % of photoinitiator or thermal initiator, and a low power blacklight or heat source. Illustrative experiments have shown that the present invention provides an efficient method of producing complex and simple triethoxy- and trimethoxysilanes, which are easily synthesized from MPTES or MPTMS and alkenes, or APTES and thiols in a single step. The reactions proceeded smoothly neat or with minimal solvent in standard borosilicate glassware to provide silanes in quantitative or near-quantitative yields and high purity (average conversions 98%; average product purities 96%). The reactions tolerate a good range of chemical functionalities and illustrative experiments show that the reactions can be scaled-up easily without sacrificing product yield or purity. Illustrative experiments also suggest that the present invention can be used to produce silanes at low costs on a pilot or even industrial scale. All of the silanes synthesized in the illustrative experiments were found to be active surface coating agents and were successfully immobilized on magnetite superparamagnetic nanoparticles (SPNs). This synthetic methodology will aid in the future development of new materials, interfaces, and devices by allowing easier access to complex and unique silane coating agents.

An advantage of synthesizing silanes using embodiments of the present invention is that reactants such as 3-mercaptopropyltrimethoxysilane (MPTMS), 3-aminopropyltriethyloxysilane (APTES) and mercaptopropyltriethoxysilane (MPTES) and many different alkenes and thiols are commercially available at low cost. Because the reactants and reagents are themselves inexpensive and only simple equipment is required, resulting in a highly economical overall process. Moreover, the ease and feasibility of scaling up the thiol-ene reaction by resynthesizing diethyl acetal triethoxysilane (designated "3" in FIG. 2) on a greater than 100 mmol scale was explored. Illustrative experiments provide evidence that the present invention is a low cost way to synthesize silanes on a commercial or industrial scale. Unless otherwise indicated, compounds identified by a numerical designation (e.g., "silane 1, silane 2" etc.) are those shown in the Figures, for example, FIGS. 2 and 3. See also, Tucker-Schwartz et al., *J. Am. Chem. Soc.* 2011, 133, 11026-11029, the contents of which are incorporated by reference.

Figure 8:
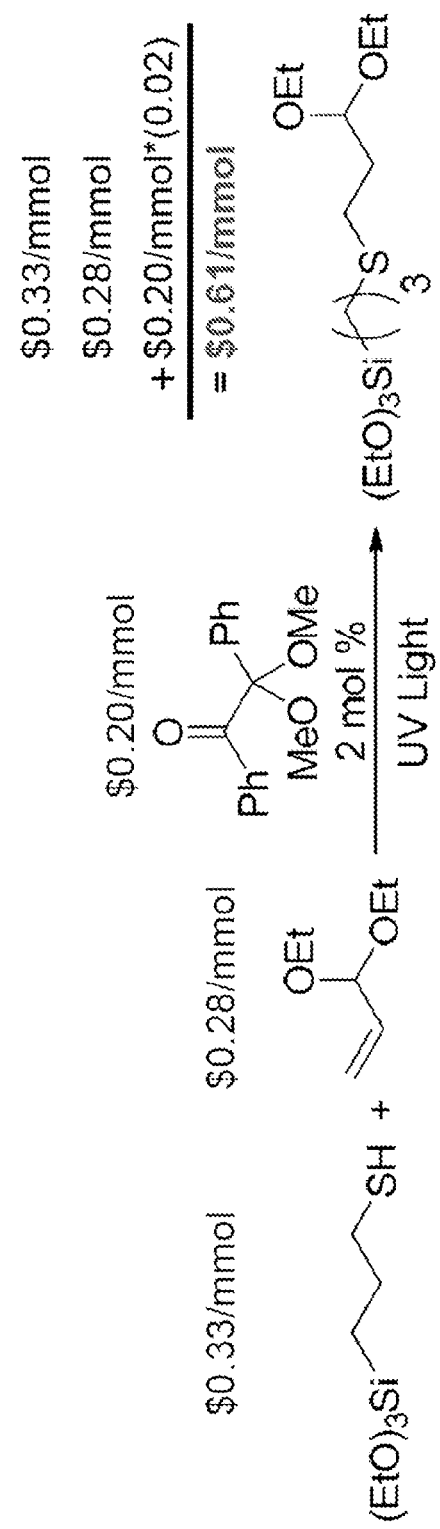
FIG. 8 is a schematic illustrating the synthesis of diethyl acetal triethoxysilane 3 and calculation for the cost of materials.
Figure 9:
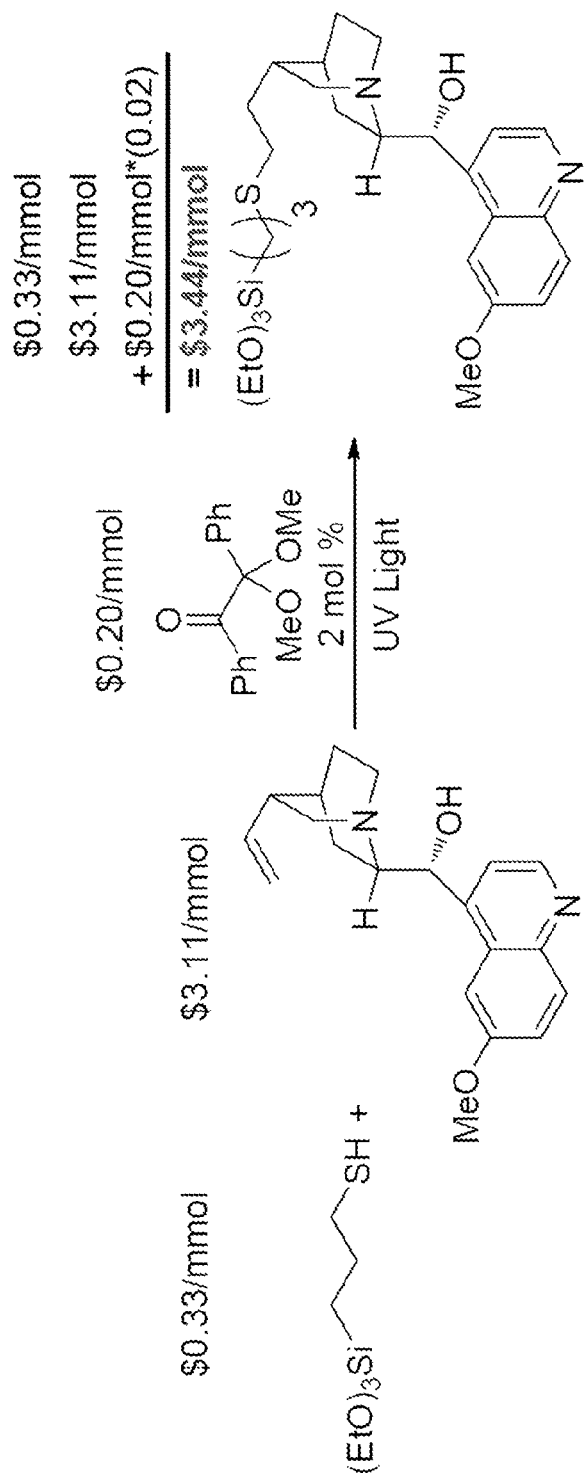
FIG. 9 is a schematic illustrating the synthesis of quinine triethoxysilane 7 and calculation for the cost of materials.

In one illustrative experiment, the reaction of acrolein diethyl acetal with MPTES was selected because of the low cost of the reactants and the similarity of product 3 to one of the few commercially available acetal-terminated trialkoxysilanes (in 2010, triethoxysilylundecanal, ethylene glycol acetal sold by GELEST Inc., cost $116.00 for 5 grams). Following irradiation of the reactants for 24 hours using two 15 W blacklights, the reaction reached more than 98% conversion, which is similar to that obtained for the 2-mmol scale reaction (FIG. 2). The product purity was 93%, slightly lower than in the small scale reaction. Most likely this was due either to misweighing the reactants or to some loss of the alkene while purging the reaction vessel. A rough estimate indicates that preparing 3 by this method costs $0.63/mmol 3. This is roughly $1/13^{th}$ the price at which the similar commercially available terminal acetal-containing triethoxysilane is sold (see, e.g., the supporting information in Tucker-Schwartz et al., *J. Am. Chem. Soc.* 2011, 133, 11026-11029, the contents of which are incorporated by reference; FIGS. 8, 9 and Example 6).

FIG. 2 shows a wide range of simple and complex exemplary alkenes that can be quantitatively or near quantitatively clicked with 3-mercaptopropyltriethoxysilane (MPTES) to produce functionalized triethoxysilane analogs. Illustrative experiments have found that only the synthesis of product 9 required a longer irradiation time and additional initiator to reach high reactant conversion. This is might be partly attributed to the increase in solution viscosity as the reaction proceeds, limiting mass transport (see, e.g., Hoyle, C. E., et al. *Angew. Chem., Int. Ed. Engl.* 2010, 49, 1540-1573). A second factor might be that product 9 absorbs at the same wavelength as the initiator, diminishing the rate of initiation as the reaction proceeds (see, e.g., the supporting information in Tucker-Schwartz et al., *J. Am. Chem. Soc.* 2011, 133, 11026-11029, the contents of which are incorporated by reference; Example 7). A variety of common functional groups were found to be well-tolerated under these reaction conditions. Because the reactions were essentially quantitative and contained only small amounts of unreacted MPTES, alkene, and decomposed photoinitiator, no chromatographic purification of the products was conducted. Importantly, the remaining non-silane impurities do not affect the ability of the triethoxysilanes to couple with surfaces, and they can be washed away after the surface modification process is complete.

The alkenes in FIG. 2 were selected as illustrative alkenes because they form silanes that are potentially useful for a variety of applications, though other alkenes not found in FIG. 2 may also be used. Tetraethylene glycol-functionalized silane 1 is similar to most graftable oligoethylenoxides that are used to minimize protein adsorption in biomedical and biosensor applications (see, e.g., Alonso, J. M., et al. *Langmuir* 2008, 24, 448-457). Thiazole-terminated silane 2 is a precursor for preparing surface-bound ionic liquids or thiazolium carbenes that are useful organocatalysts and strong metal coordinating ligands (see, e.g., Abu-Reziq, R., et al. *Adv. Synth. Catal.* 2007, 349, 2145-2150). Silanes 3 and 4 contain masked distal aldehyde and carboxylic acid groups that can be deprotected by mild acid hydrolysis and can be very effective to pattern aldehydes and carboxylic acids on planar substrates using photolithography and photoacids (see, e.g., Christman, K. L., et al. *Langmuir* 2005, 21, 8389-8393). Silane 5, while not a catalyst itself, was made to demonstrate the compatibility of this methodology with thioureas, an important class of coordinating organocatalysts (see, e.g., Takemoto, Y. *Org. Biomol. Chem.* 2005, 3, 4299-4306). Silanes 6, 7, and 8 can be coated on surfaces and then deprotected to form valuable heterogeneous catalysts (see, e.g., Shylesh, S., et al. *Angew. Chem., Int. Ed. Engl.* 2010, 49, 3428-3459). NTA silane 9 contains a ligand that is used to bind histidine-tagged proteins once the tert-butyl esters have been cleaved; it has been utilized for protein purification and as an intracellular pH-sensitive peptide delivery agent (see, e.g., Xu, C. J., et al. *J. Am. Chem. Soc.* 2004, 126, 9938-9939; June, R. K., et al. *J. Am. Chem. Soc.* 2010, 132, 10680-10682). Finally, tetra-acylated glycopyranoside silane 10 can be used after acyl deprotection to binding lectins, and has the potential to be used in cancer diagnostic tools (see, e.g., El-Boubbou, K., et al. *J. Am. Chem. Soc.* 2010, 132, 4490-4499).

MPTES was selected as an illustrative silane precursor for the initial reactions shown in FIG. 2 because of its low moisture sensitivity; however, other silane precursors may be used instead. In one exemplary implementation, as shown by the first two entries in FIG. 3, MPTES can be replaced with 3-mercaptopropyltrimethoxysilane (MPTMS) to make a more reactive trimethoxysilane coating agent. For example, illustrative experiments found that MPTES coupled smoothly to 11-undecenoic acid, with no evidence of hydrolysis of the trimethoxysilane. In other exemplary implementations, the last two entries in FIG. 3 illustrate that the mercaptosilane precursors can be replaced with allyltriethoxysilane (ATES) to cleanly couple thiol-containing compounds such as cysteine. Additionally, the silanes synthesized by the present invention can be covalently bound to magnetite superparamagnetic nanoparticles (SPNs), with the loading quantified by elemental analysis.

Figure 4:
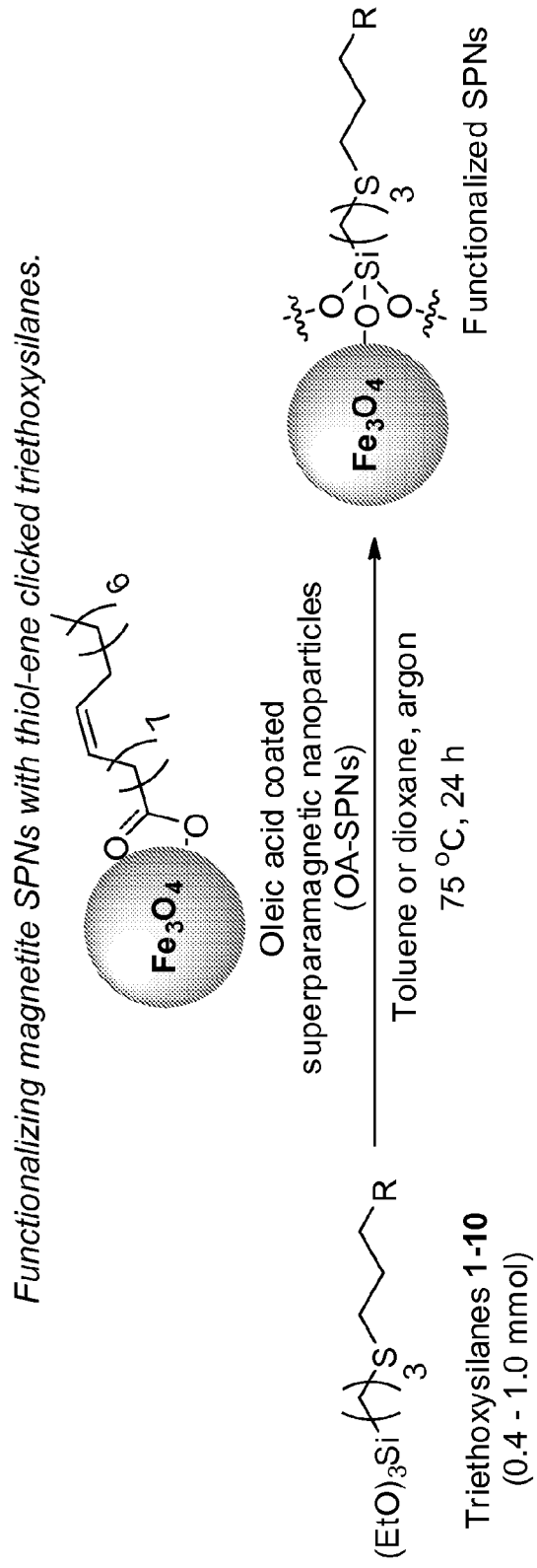
FIG. 4 is a schematic illustrating functionalization of magnetite SPNs with thiol-ene clicked triethoxysilanes.

When silanes are used as surface coating agents, it is often desirable to quantify the amount of silane that is bound to the surface. Doing so can be challenging, especially when the silanes lack a distinctive atom or functional group that can be identified spectroscopically. An advantage of the present invention is that the product silanes have at least one sulfur atom in their structure, which facilitates their quantification by elemental analysis. In illustrative experiments for demonstrating that the synthesized silanes in FIG. 2 can be used as surface coating agents, triethoxysilanes 1-10 were immobilized onto magnetite superparamagnetic nanoparticle (SPN) surfaces as shown in FIG. 4. In the illustrative experiments, oleic acid-coated SPNs were heated at 75° C. in toluene or dioxane for 24 h with 0.4 to 1 mmol of the silane. After particle isolation using a hand-held rare earth magnet and rinsing, the resulting constructs were characterized by sulfur elemental analysis and FT-IR spectroscopy. Triethoxysilanes 1-10 were found to efficiently coat SPNs. Silane loadings ranged from 0.13 to 0.79 mmol/g SPN, as determined by sulfur elemental analysis (see, e.g., Example 9). The loading variability is thought to be a consequence of differences in the silane solubilities, the varying degrees of intermolecular interactions between silanes and oleic acid coatings on SPNs, the sterics of the silane tail, and small differences in the amount of water in the solvents, as water catalyzes the silane coating process. All particles retained their superparamagnetic properties after surface modification. Aspects of such various procedures and analyses disclosed herein have been published in a technical journal, Tucker-Schwartz et al., *J. Am. Chem. Soc.* 2011, 133, 11026-11029, the contents of which are incorporated by reference.

In other illustrative experiments using the thiol-ene reaction disclosed herein, 13 different alkenes were reacted with 3-mercaptopropyltrialkoxysilane and 2-mol % photoinitiator to obtain the functionalized silanes in quantitative yields with purities ≥94%. The photochemical reactions were generally run neat using a 15-W blacklight. A range of functional groups was tolerated using this approach; even complex alkenes successfully clicked with the mercaptosilanes. To demonstrate that the synthesized silanes can be used as surface coating agents, they were coated onto iron oxide superparamagnetic nanoparticles and the loadings were quantified. Such illustrative experiments demonstrate that the thiol-ene reaction provides an easy route to prepare functional trialkoxysilanes for surface coatings and other applications.

EXAMPLES

Now, the present invention will be described in detail in reference to various examples, but should not be limited to these examples.

A variety of embodiments of the invention have been synthesized, tested and put into practice. As illustrated below, a large number of triethoxy- and trimethoxysilanes having simple or complex pendant groups have been synthesized using equimolar amounts of one alkene and one thiol, a catalytic quantity of an active radical initiator (e.g., photoinitiator, and a low power UV light). The working examples disclosed herein demonstrate that a large number of different functional groups can be coupled to alkyoxysilanes via a C—S—C linkage using the disclosed synthesis methodology and, for example, that small biomolecules (such as glucose) can be attached as pendant groups. Additionally, we have shown that embodiments of the invention allow reactions to reach >98% reactant conversion, and have average purities of ~95% without subsequent purification. Most silanes have been synthesized on a small scale (0.5-5 mmol). We also demonstrate the synthesis of two triethoxysilanes on a large scale (>100 mmol, ~37 g) using low power UV irradiation and catalytic amounts of a photoinitiator.

Example 1

Illustrative Methods and Materials Useful in Embodiments of the Invention

Ferric chloride hexahydrate ($FeCl_3 \cdot 6H_2O$), ferrous chloride tetrahydrate ($FeCl_2 \cdot 4H_2O$), ammonium hydroxide ($NH_4OH$), oleic acid, sodium sulfate ($Na_2SO_4$), magnesium sulfate ($MgSO_4$), hydrochloric acid (HCl), and sodium hydroxide (NaOH) were purchased from Fisher Scientific (Pittsburgh, Pa.). 3-mercaptopropyltriethoxysilane (MPTES), 3-mercaptopropyltrimethoxysilane (MPTMS), allyltriethoxysilane (ATES) were purchased at >95% purity from Gelest Inc. (Morrisville, Pa.). Diisopropylethylamine, potassium tert-butoxide (t-BuOK), and tetraethyleneglycol monomethyl ether were purchased from Acros Organics. Allyl bromide, 5-(2-hydroxyethyl)-4-methylthiazole, 10-undecenoic acid, di-tert-butyl dicarbonate, N,N-dimethylaminepyridine, N-Boc-trans-4-hydroxy-L-proline methyl ester, 4-penteneoic anhydride, 3-aminoquinuclidine dihydrochloride, dicyclohexylcarbodiimide (DCC), L-serine-tert-butyl ester, tert-butyl bromoacetate, benzyl hydrosulfide, 2,2-dimethoxy-1,2-diphenylethanone, Celite® 500 fine, and all other alkene substrates were purchased from Sigma Aldrich (St. Louis, Mo.). All solvents were HPLC grade and purchased from either EMD Biosciences, Inc. (Gibbstown, N.J.) or Fisher. Dry THF, dioxane, and toluene were prepared by mixing the solvent with $MgSO_4$ and filtering into hot dry glassware just prior to use. All other solvents and chemicals were used as received.

Hand-held rare-earth magnets, recycled from computer hard drives, were used to separate magnetic nanoparticles from solution. Sonication was performed using a Branson 2510 ultrasonicator. Fourier transform infrared spectroscopy (FT-IR) was performed using pressed KBr pellets, or thin liquid films between AgCl plates on a Jasco FT/IR-420. Elemental analysis was performed on a Flash 1112 series elemental analyzer (Thermo Scientific). Magnetic measurements of particles were made using a Quantum Design MPMS 5XL Super Quantum Interference Device (SQUID) magnetometer. Transmission electron microscopy (TEM) images were obtained with an 80-300 kV tunable Titan TEM/STEM. $_1$H, $_{13}$CNMR spectra were obtained using either a Bruker AV300 spectrometer, or Bruker ARX400 spectrometer with a sample changer and $CDCl_3$ or $CD_3CN$ as solvents. High resolution mass spectra were acquired on a Waters LCT Premier XE time-of-flight mass spectrometer; gas chromatography/mass spectrometry (GC/MS) was performed on a Agilent 6890-5975 GC-MS with autosampler, equipped with an HP-5 column.

Example 2

Illustrative Methods and Materials Useful for Alkene Precursor Synthesis

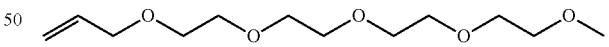

2,5,8,11,14-Pentaoxaheptadec-16-ene

An oven-dried 100 mL round bottom flask was charged with t-BuOK (13 mmol), dry THF (30 mL), purged with argon and cooled to 0° C. in an ice bath. Tetraethyleneglycol monomethyl ether (10 mmol) was then added dropwise to the solution and the reaction stirred at 0° C. for 1 h under argon. Allyl bromide (13 mmol) was added dropwise, and the solution was warmed to R.T. and allowed to stir for 24 h under argon. Deionized water (2 mL) was then added and the reaction stirred for 10 min. All liquid were then removed in vacuo and the residue redissolved in ethyl acetate (50 mL). The organic was washed three times with water (20 mL), dried over $Na_2SO_4$, filtered over Celite and then concentrated in vacuo to yield clear/light yellow oil (47%). $_1$HNMR (400 MHz, CDCl$_3$): δ=5.90 (m, 1H), 5.23 (dd, 1H, $_3J_{HHtrans}$=17.3 Hz, $_2J_{HHgem}$=1.7 Hz), 5.15 (dd, 1H, $_3J_{HH}$=10.4 Hz, $_2J_{HHgem}$=1.5 Hz), 4.00 (dd, 2H, $_3J_{HH}$=5.89 Hz, $_4J_{HH}$=1.5 Hz), 3.65 (m, 12H), 3.59 (m, 2H), 3.53 (m, 2H), 3.36 (s 3H) ppm. $_{13}$CNMR (400 MHz, CDCl$_3$): δ=134.8, 117.0, 72.2, 71.9, 70.6, 70.6, 70.6, 70.5, 69.4, 59.0 ppm. HRMS-ESI: Calculated [M+Na]+: 271.1516. found: 271.1516.

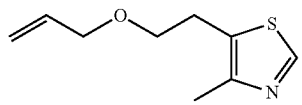

5-(2-(Allyloxy)ethyl)-4-methylthiazole

An oven-dried 100 mL round bottom flask was charged with t-BuOK (20.8 mmol), dry THF (25 mL), purged with argon and cooled to 0° C. in an ice bath. 5-(2-Hydroxyethyl)-4-methylthiazole (16 mmol) was then added dropwise to the solution and the reaction stirred at 0° C. for 1 h under argon. Allyl bromide (20.8 mmol) was added dropwise, and the solution was warmed to R.T. and allowed to stir for 20 h under argon. Deionized water (4 mL) was then added and the reaction stirred for 10 min. All liquid were then removed in vacuo and the residue redissolved in ethyl acetate (50 mL). The organic phase was washed three times with water (20 mL), dried over Na$_2$SO$_4$, filtered over Celite, and then concentrated in vacuo to yield a yellow oil (96%). $_1$HNMR (400 MHz, CDCl$_3$): δ=8.52 (s, 1H), 5.89 (m, 1H), 5.23 (dd, 1H, $_3J_{HHtrans}$=17.4 Hz, $_2J_{HHgems}$=1.8 Hz), 5.13 (dd, 1H, $_3J_{HHcis}$=10.3 Hz, $_2J_{HHgems}$=1.6 Hz), 3.96 (dt, 2H, $_3J_{HH}$=5.7 Hz, $_4J_{HH}$=1.4 Hz), 3.57 (t, 2H, $_3J_{HH}$=6.9 Hz), 2.99 (t, 2H, $_3J_{HH}$=6.9 Hz), 2.37 (s, 3H) ppm. $_{13}$CNMR (400 MHz, CDCl$_3$): δ=149.6, 149.2, 134.5, 127.9, 17.0, 71.9, 70.0, 27.0, 14.9 ppm. HRMS-ESI: Calculated [M+H]+: 184.0791. found: 184.0787.

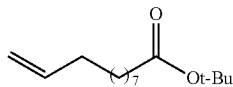

tert-Butyl undec-10-enoate

An oven-dried 50 mL round bottom flask was charged with 10-undeceneoic acid (5 mmol), di-tert-butyl dicarbonate (10 mmol) and tert-butanol (10 mL). N,N-dimethylaminopyridine (1.5 mmol) was added to the stirred mixture and the reaction was allowed to stir for 20 h at R.T. The reaction mixture was concentrated in vacuo and the residue purified by silica gel chromatography using ethyl acetate/hexanes (2:8) to afford the product as a light yellow oil (58%). R$_f$=0.98. $_1$HNMR (400 MHz, CDCl$_3$): δ=5.81 (m, 1H), 4.96 (dq, 1H, $_3J_{HH}$=17.1 Hz, $_4J_{HH}$=1.6 Hz), 4.91 (dq, 1H, $_3J_{HH}$=10.2 Hz, $_4J_{HH}$=1.2 Hz), 2.19 (t, 2H, $_3J_{HH}$=7.7 Hz), 2.02 (q, 2H, $_3J_{HH}$=7.0 Hz), 1.28-1.56 (m, 21H) ppm. $_{13}$CNMR (400 MHz, CDCl$_3$): δ=173.3, 139.2, 114.1, 79.9, 35.6, 33.8, 29.3, 29.2, 29.0, 28.9, 28.1, 25.1 ppm. GC/MS (EI): Calculated [M-C$_4$H$_9$]+: 184.1. found: 184.1.

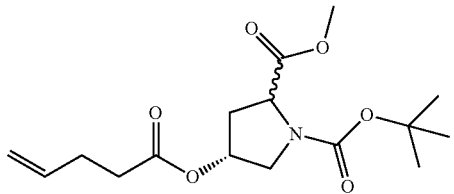 [SMILES: C=CCCC(=O)O[C@@H]1CC(C(=O)OC)N(C(=O)OC(C)(C)C)C1]

N-Boc 2-methyl (4R)-4-(pent-4-enoyloxy)pyrrolidine-1,2-dicarboxylate

An oven-dried 50 mL round bottom flask was charged with N-Boc-trans-4-hydroxy-L-proline methyl ester (1 mmol), N,N-dimethylaminopyridine (0.15 mmol), pyridine (3 mmol), dry acetonitrile (5 mL), and placed under an argon atmosphere. 4-Pentenoic anhydride (3 mmol) was then added dropwise and the reaction was warmed to 50° C. and stirred under argon for 44 h. The reaction mixture was then concentrated in vacuo, and the residue dissolved in THF (5 mL), deionized water (3 mL), pyridine (0.5 mL) and allowed to stir an additional 24 h at 50° C. The reaction mixture was then concentrated in vacuo, the residue dissolved in DCM (20 mL), and the DCM washed 1 M HCl (15 mL), water (15 mL), 1 M NaOH (15 mL), and finally with water (15 mL). The organic was dried over Na$_2$SO$_4$, filtered over Celite, and then concentrated in vacuo to yield a yellow oil (71%). Diastereomeric mixture (59:41). $_1$HNMR (400 MHz, CDCl$_3$): δ=5.80 (m, 1H), 5.29 (m, 1H), 5.03 (m, 2H), 4.39 (dt, 1H, $_3J_{HH}$=8.7 Hz), 3.71 (s, 3H), 3.70-3.05 (m, 2H), 2.37 (m, 5H), 2.17 (m, 1H), 1.46 (s, 3H), 1.41 (s, 6H) ppm. $_{13}$CNMR (400 MHz, CDCl$_3$): δ=172.9, 172.7, 172.3, 172.1, 154.0, 153.3, 136.2, 115.6, 80.3, 72.6, 71.8, 57.8, 57.4, 52.2, 52.0, 51.9, 36.5, 35.5, 33.2, 30.2, 29.6, 28.7, 28.2, 28.1 ppm. HRMS-ESI: Calculated [M+Na]+: 350.1574. found: 350.1568.

N-(quinuclidin-3-yl)undec-10-enamide

An oven-dried 50 mL round bottom flask was charged with 3-aminoquinuclidine dihydrochloride (2 mmol), 10-undecenoic acid (2 mmol), N,N-dimethylaminopyridine (0.3 mmol), diisopropylethylamine (4 mmol), and dry DMF (15 mL). The flask was purged with argon and cooled to 0° C. in an ice bath. Dicyclohexycarbodiimide (2.2 mmol) was then add to the solution, the flask repurged with argon, and the mixture warmed to R.T. and stirred for 46 h. The reaction mixture was concentrated in vacuo and 30 ml diethyl ether added to the residue. The solid was filtered off over Celite and the organic phase concentrated in vacuo. The residue was purified by silica gel chromatography using ethyl acetate/hexanes (3:7) to afford the product as a white solid (23%). R$_f$=0.44. $_1$HNMR (400 MHz, CDCl$_3$): δ=5.73 (m, 1H), 4.93 (dd, 1H, $_3J_{HH}$=17.0 Hz, $_4J_{HH}$=1.5 Hz), 4.87 (d, 1H, $_3J_{HH}$=10.3 Hz), 3.71 (m, 1H), 2.10 (t, 2H, $_3J_{HH}$=7.8 Hz), 1.97

(q, 2H, $_3J_{HH}$=7.3 Hz), 1.85 (m, 2H), 1.54-1.68 (m, 5H), 1.02-1.34 (m, 15H) ppm. $_{13}$CNMR (400 MHz, CDCl$_3$): δ=172.2, 139.1, 114.1, 48.6, 48.0, 37.0, 34.0, 33.7, 33.2, 29.3, 29.2, 29.0, 28.8, 25.9, 25.7, 25.5, 25.0, 24.9 ppm. HRMS-ESI: Calculated [M-C$_2$H$_2$]+: 266.2358. found: 266.2474.

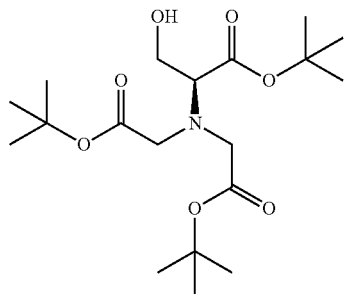 [SMILES: CC(C)(C)OC(=O)CN(CC(=O)OC(C)(C)C)[C@@H](CO)C(=O)OC(C)(C)C]

(S)-tert-Butyl-2-di(tert-butyloxycarbonylmethyl)amino-3-hydroxypropanoate

This material was prepared following a previously reported protocol (Meunier, S.; Cristau, P.; Taran, F. *Synth. Commun.* (2005), 35, 2415-2425). An oven-dried 100 mL round bottom flask was charged with L-serine tert-butyl ester hydrochloride (4 mmol), diisopropylethylamine (24 mmol), and acetonitrile (25 mL). tert-butyl bromoacetate (16 mmol) was then added dropwise and the entire mixture refluxed in air for 24 h. The reaction mixture was concentrated in vacuo and ethyl acetate (40 mL) added and the resulting precipitate filtered off over Celite. The ethyl acetate was then concentrated in vacuo and the residue purified by silica gel chromatography using ethyl acetate/hexanes (2:8) to afford the product as a light yellow solid (68%). $R_f$=0.56. $_1$HNMR (400 MHz, CDCl$_3$): δ=4.21 (d, 1H, $_3J_{HH}$=10.9 Hz), 3.69 (td, 1H, $_2J_{HH}$=10.8 Hz, $_3J_{HH}$=13.6 Hz), 3.42 (m, 6H), 1.40 (s, 27H) ppm. $_{13}$CNMR (400 MHz, CDCl$_3$): δ=171.3, 107.2, 81.7, 81.3, 68.2, 60.1, 54.9, 28.1, 28.0 ppm. HRMS-ESI: Calculated [M+H]+: 390.2488. found: 390.2470.

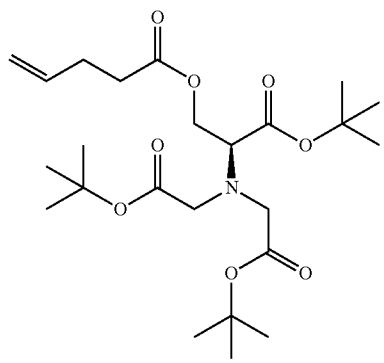 [SMILES: C=CCCC(=O)OC[C@@H](C(=O)OC(C)(C)C)N(CC(=O)OC(C)(C)C)CC(=O)OC(C)(C)C]

(S)-tert-Butyl-2-di(tert-butyloxycarbonylmethyl)amino-3-(pent-4-enoyloxy)-propanoate An oven-dried 50 mL round bottom flask was charged with (S)-tert-butyl-2-di(tert-butyloxycarbonylmethyl)amino-3-hydroxypropanoate (1 mmol), N,N-dimethylaminopyridine (0.3 mmol), diisopropylethylamine (3 mmol), acetonitrile (5 mL), and purged with argon. 4-pentenoic anhydride (3 mmol) was then slowly added dropwise and the reaction mixture stirred under argon at 55° C. for 42 h. The reaction mixture was concentrated in vacuo and the residue dissolved in THF (5 mL), deionized water (1 mL), pyridine (0.5 mL), capped, and stirred at 55° C. for 24 h. Solvents were concentrated in vacuo and the residue purified by silica gel chromatography using ethyl acetate/hexanes (1:9) to afford the product as a light yellow oil (96%). $R_f$=0.49. $_1$HNMR (400 MHz, CDCl$_3$): δ=5.80 (m, 1H), 5.05 (dq, 1H, $_3J_{HH}$=17.2 Hz, $_4J_{HH}$=1.6 Hz), 4.97 (dq, 1H, $_3J_{HH}$=10.2 Hz, $_4J_{HH}$=1.4 Hz), 4.42 (dd, 1H, $_2J_{HH}$=10.9 Hz, $_3J_{HH}$=5.9 Hz), 4.29 (dd, 1H, $_2J_{HH}$=11.2 Hz, $_3J_{HH}$=6.7 Hz), 3.69 (t, 1H, $_3J_{HH}$=5.6 Hz), 3.55 (s, 2H), 3.54 (s, 2H), 2.36 (m, 4H), 1.45 (s, 9H), 1.44 (s, 18H) ppm. $_{13}$CNMR (400 MHz, CDCl$_3$): δ=172.4, 170.6, 169.6, 136.6, 115.5, 81.7, 80.8, 63.8, 63.5, 54.3, 33.4, 28.7, 28.1 ppm. HRMS-ESI: Calculated [M+H]+: 472.2905. found: 472.2924.

Example 3

Illustrative Methods and Materials Useful for Triethoxysilane Synthesis

General Procedure.

A cooled oven-dried 10-mL round bottom was charged with MPTES (1 equiv.), alkene (1 equiv.) and 2 mol % 2,2-dimethoxy-1,2-diphenylethanone (0.02 equiv.), known commercially as Irgacure®651. The reaction was run neat unless the alkene did not fully dissolve, in which case a tiny amount of dry chloroform or methanol was added. The reaction mixture was then capped with a septum and purged briefly with argon or nitrogen. The flask was placed next to an 15 W, 18"-long blacklight having a total UV output of 2.6 W and $λ_{max}$=368 nm. The flask was positioned so that one side rested against the center of the bulb. The UV flux at $λ_{max}$=368 nm was measured to be 30% attenuated after passing through standard thickness Pyrex glass beaker. Both the flask and blacklight were wrapped in aluminum foil and the reaction mixture irradiated on average for 24 h with gentle stirring to yield product silanes in high purity. If solvent was added to the reaction, it was removed in vacuo upon completion of the reaction. Product conversion and purity were determined by $_1$HNMR or GC/MS.

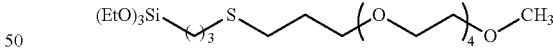

PEG Triethoxysilane (1)

Following the general procedure above, MPTES (2 mmol), 2,5,8,11,14-pentaoxaheptadec-16-ene (2 mmol), and Irgacure®651 (0.04 mmol) were mixed, purged with argon, and irradiated 24 h (>99% conversion, 96% pure). $_1$HNMR (400 MHz, CDCl$_3$): δ=3.78 (q, 2H, $_3J_{HH}$=6.7 Hz), 3.35-3.65 (m, 18H), 3.37 (s, 3H), 2.56 (t, 2H, $_3J_{HH}$=7.6 Hz), 2.52 (t, 2H, $_3J_{HH}$=7.2 Hz), 1.82 (m, 2H), 1.68 (m, 2H), 0.726 (t, $_3J_{HH}$=8.5 Hz) ppm. $_{13}$CNMR (400 MHz, CDCl$_3$): δ=70.6, 70.6, 70.6, 70.6, 70.5, 70.5, 70.2, 69.8, 59.0, 58.4, 35.2, 29.7, 28.6, 23.2, 18.3, 9.9 ppm. HRMS-ESI: Calculated [M+Na]+: 509.2575. found: 509.2552.

27

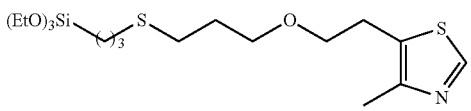

Thiazole Triethoxysilane (2)

Following the general procedure above, MPTES (5 mmol), 5-(2-(allyloxy)ethyl)-4-methylthiazole (5 mmol), and Irgacure®651 (0.1 mmol) were mixed, purged with argon, and irradiated 24 h (>99% conversion, 95% pure). $_1$HNMR (400 MHz, CDCl$_3$): δ=8.54 (s, 1H), 3.78 (q, 6H, $_3J_{HH}$=7.2 Hz), 3.56 (t, 2H, $_3J_{HH}$=6.6 Hz), 3.50 (t, 2H, $_3J_{HH}$=6.1 Hz), 2.98 (t, 2H, $_3J_{HH}$=6.4 Hz), 2.56 (t, 2H, $_3J_{HH}$=7.2 Hz), 2.50 (t, 2H, $_3J_{HH}$=7.2 Hz), 2.37 (s, 3H), 1.14 (t, 9H, $_3J_{HH}$=6.7 Hz), 0.71 (t, 2H, $_3J_{HH}$=7.7 Hz) ppm. $_{13}$CNMR (400 MHz, CDCl$_3$): δ=149.6, 149.1, 128.0, 70.6, 69.5, 58.4, 35.1, 29.8, 28.6, 27.0, 23.0, 18.3, 14.9, 9.9 ppm. HRMS-ESI: Calculated [M+H]+: 422.1850. found: 422.1850.

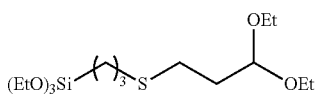

Diethyl Acetal Triethoxysilane (3)

Following the general procedure above, MPTES (2 mmol), acrolein diethyl acetal (2 mmol), and Irgacure®651 (0.04 mmol) were mixed, purged with argon, and irradiated 24 h (>99% conversion, 96% pure). $_1$HNMR (400 MHz, CDCl$_3$): δ=4.95 (t, 1H, $_3J_{HH}$=5.6 Hz), 3.80 (q, 6H, $_3J_{HH}$=7.1 Hz), 3.64 (m, 2H), 3.49 (m, 2H), 2.53 (q, 4H, $_3J_{HH}$=6.6 Hz), 1.88 (m, 2H), 1.70 (m, 2H), 1.20 (m, 15H), 0.72 (t, 2H, $_3J_{HH}$=8.1 Hz) ppm. $_{13}$CNMR (400 MHz, CDCl$_3$): δ=101.17, 61.5, 58.4, 35.2, 33.9, 27.1, 23.2, 18.3, 15.3, 9.9 ppm. HRMS-ESI: Calculated [M+Na]+: 391.1945. found: 391.1932.

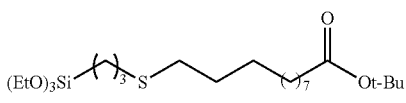

tert-Butyl Undecanoate Triethoxysilane (4)

Following the general procedure above, MPTES (2 mmol), tert-butyl undec-10-enoate (2 mmol), and Irgacure®651 (0.04 mmol) were mixed, purged with argon, and irradiated 24 h (>98% conversion, 96% pure). $_1$H NMR (400 MHz, CDCl$_3$): δ=3.81 (q, 6H, $_3J_{HH}$=6.9 Hz), 2.52 (t, 2H, $_3J_{HH}$=7.2 Hz), 2.48 (t, 2H, $_3J_{HH}$=7.2 Hz), 2.19 (t, 2H, $_3J_{HH}$=7.6 Hz), 1.68 (m, 2H), 1.56 (m, 4H), 1.43 (s, 9H), 1.36 (m, 12H), 1.22 (t, 9H, $_3J_{HH}$=7.2 Hz), 0.73 (t, 2H, $_3J_{HH}$=8.4 Hz) ppm. $_{13}$CNMR (400 MHz, CDCl$_3$): δ=173.3, 79.9, 58.4, 35.6, 35.2, 32.0, 29.8, 29.5, 29.4, 29.3, 29.2, 29.1, 29.0, 28.1, 25.1, 23.3, 18.3, 9.9 ppm. HRMS-ESI: Calculated [M+Na]+: 501.3046. found: 501.3050.

28

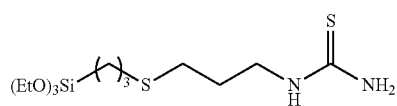

Thiourea Triethoxysilane (5)

Following the general procedure above, MPTES (2 mmol), N-allylthiourea (2 mmol), Irgacure®651 (0.04 mmol), and dry MeOH (0.6 mL) were mixed, purged with argon, and irradiated 24 h (>99% conversion, 95% pure). $_1$HNMR (400 MHz, CDCl$_3$): δ=6.61 (bs, 1H), 5.94 (bs, 1H), 3.77 (q, 6H, $_3J_{HH}$=6.6 Hz), 3.51 (bs, 1H), 2.51 (q, 4H, $_3J_{HH}$=7.3 Hz), 2.16 (s, 2H), 1.77 (m, 2H), 1.62 (m, 2H), 1.59 (t, 9H, $_3J_{HH}$=7.4 Hz), 0.68 (t, 2H, $_3J_{HH}$=8.2 Hz) ppm. $_{13}$CNMR (400 MHz, CDCl$_3$): δ=182.9, 58.2, 34.7, 28.9, 22.9 ppm. HRMS-ESI: Calculated [M+Na]+: 377.1365. found: 377.1368.

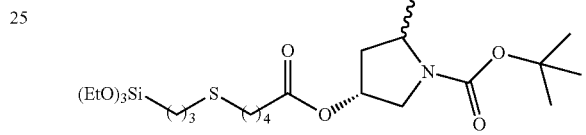

Mix of diestereomers (59:41)

N-Boc-(4R)-4-hydroxy-L-proline methyl ester triethoxysilane (6)

Following the general procedure above, MPTES (0.66 mmol), N-Boc 2-methyl (4R)-4-(pent-4-enoyloxy)pyrrolidine-1,2-dicarboxylate (0.66 mmol), and Irgacure®651 (0.013 mmol) were mixed, purged with argon, and irradiated 24 h (96% conversion, 94% pure). $_1$HNMR (400 MHz, CDCl$_3$): δ=5.28 (s, 1H), 4.34 (dt, 1H, $_3J_{HH}$=8.3 Hz), 3.82 (q, 6H, $_3J_{HH}$=6.9 Hz), 3.49-3.74 (m, 5H), 2.51 (q, 4H, $_3J_{HH}$=7.3 Hz), 2.36 (m, 1H 2.32 (t, 2H, $_3J_{HH}$=7.7 Hz), 2.19, (m, 1H), 1.68 (m, 6H), 1.45 (s, 3H), 1.41 (s, 6H), 1.22 (t, 9H, $_3J_{HH}$=7.2 Hz), 0.73 (t, 2H, $_3J_{HH}$=8.0) ppm. $_{13}$CNMR (400 MHz, CDCl$_3$): δ=173.1, 172.8, 172.7, 154.2, 153.5, 80.5, 72.5, 71.8, 58.4, 57.9, 57.5, 52.3, 52.2, 52.1, 52.0, 36.6, 35.6, 35.1, 33.8, 31.4, 29.0, 28.3, 28.2, 24.0, 23.2, 18.3, 9.9 ppm. HRMS-ESI: Calculated [M+Na]+: 588.2639. found: 588.2649.

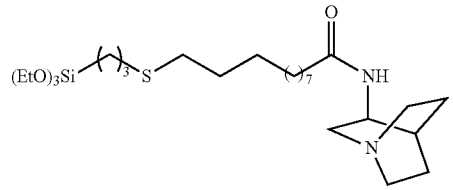

Quinuclidine Triethoxysilane (7)

Following the general procedure above, MPTES (0.41 mmol), N-(quinuclidin-3-yl)undec-10-enamide (0.41 mmol), Irgacure®651 (0.008 mmol), and dry CHCl$_3$ (0.5 mL) were mixed, purged with argon, and irradiated 24 h (>98% conversion, 96% pure). $_1$HNMR (400 MHz, CDCl$_3$): δ=5.34 (s, 1H), 3.80 (m, 6H), 2.52 (t, 2H, $_3J_{HH}$=7.5 Hz), 2.48 (t, 2H, $_3J_{HH}$=7.5 Hz), 2.11 (t, 2H, $_3J_{HH}$=7.8 Hz), 1.57-1.89 (m, 12H), 1.23 (m, 26H), 0.73 (t, 2H, $_3J_{HH}$=8.2 Hz) ppm. $_{13}$CNMR (400 MHz, CDCl$_3$): δ=172.1, 129.1, 77.2, 67.1, 58.4, 58.2, 48.0, 37.1, 35.2, 33.3, 32.0, 29.8, 29.5, 29.4, 29.3, 29.2, 29.0, 25.9, 25.6, 24.9, 23.2, 18.3, 9.9 ppm. HRMS-ESI: Calculated [M-C$_3$H$_6$NO]+: 458.3124. found: 458.3134.

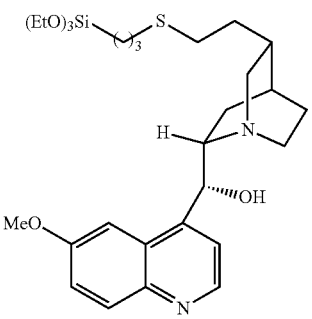

Quinine Triethoxysilane (8)

Following the general procedure above, MPTES (1 mmol), quinine (1 mmol), Irgacure®651 (0.02 mmol), and dry CHCl$_3$ (1 mL) were mixed, purged with argon, and irradiated 27 h (>98% conversion, 96% pure). $_1$HNMR (400 MHz, CDCl$_3$): δ=8.63 (d, 1H, $_3J_{HH}$=4.6 Hz), 7.95 (d, 1H, $_3J_{HH}$=9.2 Hz), 7.47 (d, 1H, $_3J_{HH}$=5.1 Hz), 7.31 (dd, 1H, $_3J_{HH}$=9.2 Hz, $_4J_{HH}$=2.6 Hz), 7.22 (d, 1H, $_4J_{HH}$=2.0 Hz), 5.51 (s, 1H), 3.98 (s, 3H), 3.78 (q, 6H, $_3J_{HH}$=7.1 Hz), 3.58 (bs, 1H), 3.42 (bs, 1H), 3.06 (m, 2H), 2.65 (m, 1H), 2.45 (t, 2H, $_3J_{HH}$=7.1 Hz), 2.39 (t, 2H, $_3J_{HH}$=7.1 Hz), 1.42-1.75 (m, 10H), 1.19 (t, 9H, $_3J_{HH}$=6.6 Hz), 0.67 (t, 2H, $_3J_{HH}$=8.2 Hz) ppm. $_{13}$CNMR (400 MHz, CDCl$_3$): δ=157.8, 147.6, 144.3, 131.6, 126.6, 121.5, 118.4, 117.5, 101.3, 77.2, 72.0, 59.8, 58.4, 43.2, 35.2, 34.7, 34.7, 30.0, 28.2, 25.7, 23.2, 21.7, 18.3, 9.9 ppm. HRMS-ESI: Calculated [M+H]+: 563.2969. found: 563.2977.

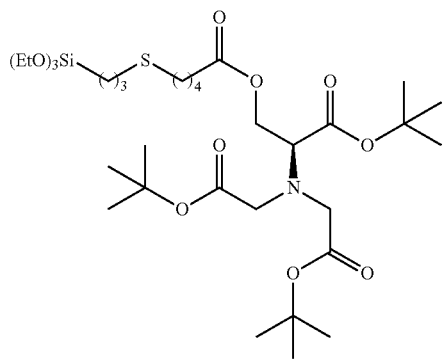

Nitrilotriacetate (NTA) Triethoxysilanesilane (9)

Following a similar procedure to the one described above, MPTES (0.5 mmol), (S)-tert-butyl-2-di(tert-butyloxycarbonylmethyl)amino-3-(pent-4-enoyloxy)propanoate (0.5 mmol), and Irgacure®651 (0.015 mmol, 3 mol %) were mixed, purged with argon, and then gently warmed in an oil bath until the Irgacure®651 dissolved. The mixture was then irradiated 45 h. Following, an additional amount of Irgacure®651 (0.01 mmol, 2 mol %) was added to the reaction, the flask purged, and the mixture irradiated an additional 22 h (94% conversion, 90% pure). $_1$HNMR (400 MHz, CDCl$_3$): δ=4.41 (dd, 1H, $_2J_{HH}$=10.9 Hz, $_3J_{HH}$=5.8 Hz), 4.27 (dd, 1H, $_2J_{HH}$=10.9 Hz, $_3J_{HH}$=6.9 Hz), 3.81 (q, 6H, $_3J_{HH}$=6.9 Hz), 3.68 (t, 1H, $_3J_{HH}$=6.6 Hz), 3.54 (d, 3H, $_4J_{HH}$=2.8 Hz), 2.50 (m, 4H), 2.30 (t, 2H, $_3J_{HH}$=7.5 Hz), 1.57-1.71 (m, 6H), 1.45 (m, 28H), 1.21 (t, 9H, $_3J_{HH}$=7.1 Hz), 0.72 (t, 2H, $_3J_{HH}$=8.3 Hz) ppm. $_{13}$CNMR (400 MHz, CDCl$_3$): δ=172.7, 170.5, 169.6, 81.8, 80.8, 63.8, 63.4, 58.4, 54.2, 35.1, 33.6, 31.5, 29.1, 28.1, 24.0, 23.2, 18.3, 9.9 ppm. HRMS-ESI: Calculated [M+H]+: 710.3964. found: 710.3981 ppm.

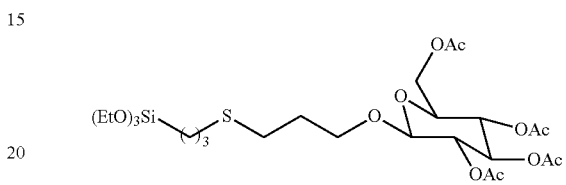

Tetra-O-acetyl-β-D-glucopyranoside triethoxysilane (10)

Following the general procedure above, MPTES (1 mmol), allyl-tetra-O-acetyl-β-D-glucopyranoside (1 mmol), Irgacure®651 (0.02 mmol), and dry CHCl$_3$ (0.6 mL) were mixed, purged, and irradiated 25 h (>99% conversion, 97% pure). $_1$HNMR (400 MHz, CDCl$_3$): δ=5.30 (s, 2H), 5.20 (t, 1H, $_3J_{HH}$=8.9 Hz), 5.07 (t, 1H, $_3J_{HH}$=9.5 Hz), 4.97 (t, 1H, $_3J_{HH}$=8.9 Hz), 4.50 (d, 1H, $_3J_{HH}$=8.9 Hz), 4.28 (dd, 1H, $_3J_{HH}$=12.5 Hz, $_3J_{HH}$=4.8 Hz), 4.14 (dd, 1H, $_3J_{HH}$=12.5 Hz, $_3J_{HH}$=2.4 Hz), 3.70 (dt, 1H, $_3J_{HH}$=10.1 Hz, $_3J_{HH}$=5.4 Hz), 3.82 (q, 6H, $_3J_{HH}$=7.2 Hz), 3.62 (m, 2H), 2.53 (q, 4H, $_3J_{HH}$=7.7 Hz), 2.08 (s, 3H), 2.04 (s, 3H), 2.02 (s, 3H), 2.00 (s, 3H), 1.80 (m, 2H), 1.67 (m, 2H), 1.22 (t, 9H, $_3J_{HH}$=7.1 Hz) 0.73 (t, 2H, $_3J_{HH}$=8.3 Hz) ppm. $_{13}$CNMR (400 MHz, CDCl$_3$): δ=170.7, 170.3, 169.4, 169.3, 101.0, 72.9, 71.8, 71.3, 68.5, 62.0, 58.4, 53.4, 53.1, 29.4, 28.2, 23.2, 20.8, 20.7, 20.6, 20.6, 18.3, 10.0 ppm. HRMS-ESI: Calculated [M+Na]+: 422.1850. found: 422.1850.

Example 4

Illustrative Methods and Materials Useful for Silane Synthesis Using MPTMS or Thiol/Ates General Procedure.

A cooled oven-dried 10-mL round bottom was charged with either MPTMS, alkene (1 equiv.) and 2 mol % Irgacure®651, or ATES (1 equiv.), or thiol (1 equiv.) and 2 mol % Irgacure®651. The reaction was run neat unless one of the reactants did not fully dissolve; in which case a tiny amount of dry chloroform, or methanol was added. The reaction mixture was then capped with a septum and purged briefly with argon or nitrogen. The flask was placed next to an 18" W blacklight, with total UV output of 2.6 W and λ$_{max}$=368 nm, so that the flask's side rested against the center of the bulb. The UV flux at λ$_{max}$=368 nm was measured to be attenuated ~30% after passing through standard thickness Pyrex glass. Both the flask and UV blacklight were wrapped in aluminum foil and the reaction mixture irradiated for 24 hours with gentle stirring to yield products in high purity. If solvent was added to the reaction, it was removed upon reaction completion in vacuo.

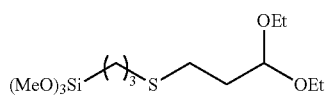

Acetal Trimethoxysilane (11)

Following the general procedure above, MPTMS (2 mmol), acrolein diethyl acetal (2 mmol), Irgacure®651 (0.04 mmol), were mixed, purged, and irradiated 24 h (>99% conversion, 96% pure). $_1$HNMR (400 MHz, CDCl$_3$): δ=4.59 (t, 1H, $_3J_{HH}$=5.5 Hz), 3.64 (m, 2H), 3.54 (s, 9H), 3.49 (m, 2H), 2.52 (q, 4H, $_3J_{HH}$=7.5 Hz), 1.86 (m, 2H), 1.69 (m, 2H), 1.19 (t, 6H, $_3J_{HH}$=7.0 Hz), 0.74 (t, 2H, $_3J_{HH}$=8.1 Hz) ppm. $_{13}$CNMR (400 MHz, CDCl$_3$): δ=101.7, 61.5, 50.5, 35.1, 33.8, 27.1, 22.9, 15.3, 8.6 ppm. HRMS-ESI: Calculated [M+Na]+: 349.1475. found: 349.1478.

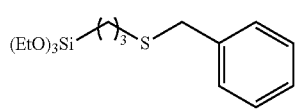

Undecanoic Acid Trimethoxysilane (12)

Following the general procedure above, MPTMS (2.5 mmol), 10-undecenoic acid (2.5 mmol), Irgacure®651 (0.05 mmol), and dry CHCl$_3$ (0.5 mL) were mixed, purged, and irradiated 24 h (>99% conversion, 96% pure). $_1$HNMR (400 MHz, CDCl$_3$): δ=3.56 (s, 9H), 2.50 (m, 4H), 2.34 (t, 2H, $_3J_{HH}$=7.8 Hz), 1.60 (m, 6H), 1.32 (m, 12H), 0.75 (t, 2H, $_3J_{HH}$=8.1 Hz) ppm. $_{13}$CNMR (400 MHz, CDCl$_3$): δ=179.5, 117.7, 50.5, 35.1, 34.0, 32.0, 29.7, 29.4, 29.3, 29.0, 28.9, 24.7, 23.0, 8.6 ppm. HRMS-ESI: Calculated [M−H]−: 379.1980. found: 379.1992.

Benzyl Triethoxysilane (13)

Following the general procedure above, ATES (2 mmol), benzyl hydrosulfide (2 mmol), Irgacure®651 (0.04 mmol), were mixed, purged, and irradiated 24 h (>99% conversion, 97% pure). $_1$HNMR (400 MHz, CDCl$_3$): δ=7.30 (m, 4H), 7.23 (m, 1H), 3.80 (q, 6H, $_3J_{HH}$=7.0 Hz), 3.70 (s, 2H), 2.44 (t, 2H, $_3J_{HH}$=7.3 Hz), 1.66 (m, 2H), 1.22 (t, 9H, $_3J_{HH}$=7.0 Hz), 0.70 (t, 2H, $_3J_{HH}$=8.3 Hz) ppm. $_{13}$CNMR (400 MHz, CDCl$_3$): δ=138.7, 128.8, 128.4, 126.9, 58.4, 36.1, 34.4, 22.8, 18.3, 9.9 ppm. HRMS-ESI: Calculated [M−C$_4$H$_9$O]+: 255.0870. found: 255.0874.

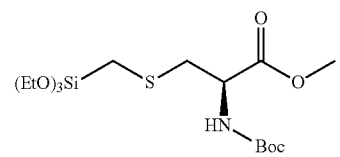

Boc-cysteine-OMe Triethoxysilane (14)

Following the general procedure above, ATES (2 mmol), N-(tert-butoxycarbonyl)-L-cysteine methyl ester (2 mmol), Irgacure®651 (0.04 mmol), were mixed, purged, and irradiated 24 h (>99% conversion, 97% pure). $_1$HNMR (400 MHz, CDCl$_3$): δ=5.43 (d, 1H, $_3J_{HH}$=7.7 Hz), 4.51 (q, 1H, $_2J_{HH}$=14.5 Hz, $_3J_{HH}$=4.9 Hz), 3.80 (q, 6H, $_3J_{HH}$=7.0 Hz), 3.74 (s, 3H), 2.93 (d, 2H, $_3J_{HH}$=4.6 Hz), 2.52 (t, 2H, $_3J_{HH}$=7.3 Hz), 1.65 (m, 2H), 1.43 (s, 9H), 1.20 (t, 9H, $_3J_{HH}$=6.6 Hz), 0.69 (t, 2H, $_3J_{HH}$=8.4 Hz) ppm. $_{13}$CNMR (400 MHz, CDCl$_3$): δ=171.6, 155.1, 80.0, 58.3, 53.2, 52.4, 35.6, 34.3, 28.3, 23.1, 18.3, 9.8 ppm. HRMS-ESI: Calculated [M+H]+: 440.2138. found: 440.2123.

Example 5

Illustrative Methods and Materials Useful for the Large-Scale Synthesis of Compounds 3 and 12

FIG. 7 shows images of a setup for large-scale synthesis of 3 and 12: a) prior to, and b) during reaction. c) Image of reaction tube containing product 3 after the reaction was complete. To synthesize 3 a cooled oven-dried Pyrex glass tube (7.5" tall, 1" diameter) with a 29/42 joint was charged with MPTES (107 mmol), acrolein diethyl acetal (107 mmol), Irgacure®651 (2.1 mmol), and then capped with a septum purged briefly with argon. The small tube diameter made it possible for the maximum amount of light to illuminate the reaction mixture. The tube was placed next to two 15 W, 18" long blacklights, each having a total UV output of 2.6 W (λ$_{max}$=368 nm). The tube was positioned so that each blacklight just rested against each side of the tube (see FIG. 7). The flask and blacklights were wrapped in aluminum foil and the reaction mixture irradiated for 24 h with gentle stirring to yield product silanes in high purity (>99% conversion, 93% pure). $_1$HNMR (400 MHz, CDCl$_3$): δ=4.95 (t, 1H, $_3J_{HH}$=5.6 Hz), 3.80 (q, 6H, $_3J_{HH}$=7.1 Hz), 3.64 (m, 2H), 3.49 (m, 2H), 2.53 (q, 4H, $_3J_{HH}$=6.6 Hz), 1.88 (m, 2H), 1.70 (m, 2H), 1.20 (m, 15H), 0.72 (t, 2H, $_3J_{HH}$=8.1 Hz) ppm. $_{13}$CNMR (400 MHz, CDCl$_3$): δ=101.17, 61.5, 58.4, 35.2, 33.9, 27.1, 23.2, 18.3, 15.3, 9.9 ppm.

To synthesize 12 a cooled oven-dried Pyrex glass tube (7.5" tall, 1" diameter) with a 29/42 joint was charged with MPTMS (100 mmol), 10-undecenoic acid (100 mmol), Irgacure®651 (2.0 mmol), and then capped with a septum purged briefly with argon. The small tube diameter made it possible for the maximum amount of light to illuminate the reaction mixture. The tube was placed next to two 15 W, 18" long blacklights, each having a total UV output of 2.6 W (λ$_{max}$=368 nm). The tube was positioned so that each blacklight just rested against each side of the tube (see FIG. 7). The flask and blacklights were wrapped in aluminum foil and the reaction mixture irradiated for 24 h with gentle stirring to yield product silanes in high purity (>99% conversion, 96% pure). $_1$HNMR (400 MHz, CDCl$_3$): δ=3.56 (s, 9H), 2.50 (m, 4H), 2.34 (t, 2H, $_3J_{HH}$=7.8 Hz), 1.60 (m, 6H), 1.32 (m, 12H), 0.75 (t, 2H, $_3J_{HH}$=8.1 Hz) ppm. $_{13}$CNMR (400 MHz, CDCl$_3$):

δ=179.5, 117.7, 50.5, 35.1, 34.0, 32.0, 29.7, 29.4, 29.3, 29.2, 29.0, 28.9, 24.7, 23.0, 8.6 ppm.

Example 6

Cost Analysis for Synthesizing Triethoxysilane Compounds 3 and 7

The estimates provided here of the material cost to produce triethoxysilanes 3 and 7 via the thiol-ene reaction were simplified by only considering the cost of the chemicals. [The blacklights, stir plate, glassware, and energy required to power the lamps were not included because the equipment is reusable and the blacklights we used are very inexpensive.] The cost estimates for producing 3 and 7 per mmol material are shown in FIGS. 8 and 9, respectively. Starting materials to prepare 3 and 7 included 25 g acrolein diethyl acetal (≥96%), 5 g quinine (suitable for fluorescence, anhydrous, ≥98.0%), 50 g 2,2-dimethoxy-1,2-diphenylethanone (>99%) purchased from SIGMA ALDRICH, and 25 g MPTES (≥95%) purchased from GELEST Inc.

The estimated cost to prepare 3 is $0.61/mmol 3. The retail price of the chemically similar, commercially available triethoxysilylundecanal ethylene glycol acetal (GELEST catalog #: SIT8194.5) is 13 times higher. The estimated cost to prepare 7 is $3.44/mmol. For comparison, the price of (R)—N-triethoxysilylpropyl quinine urethane (Gelest catalog #: SIT8192.4) is 4 times higher.

Example 7

UV-Visible Spectra of Silane Compound 9 and Photoinitiator

Figure 10:
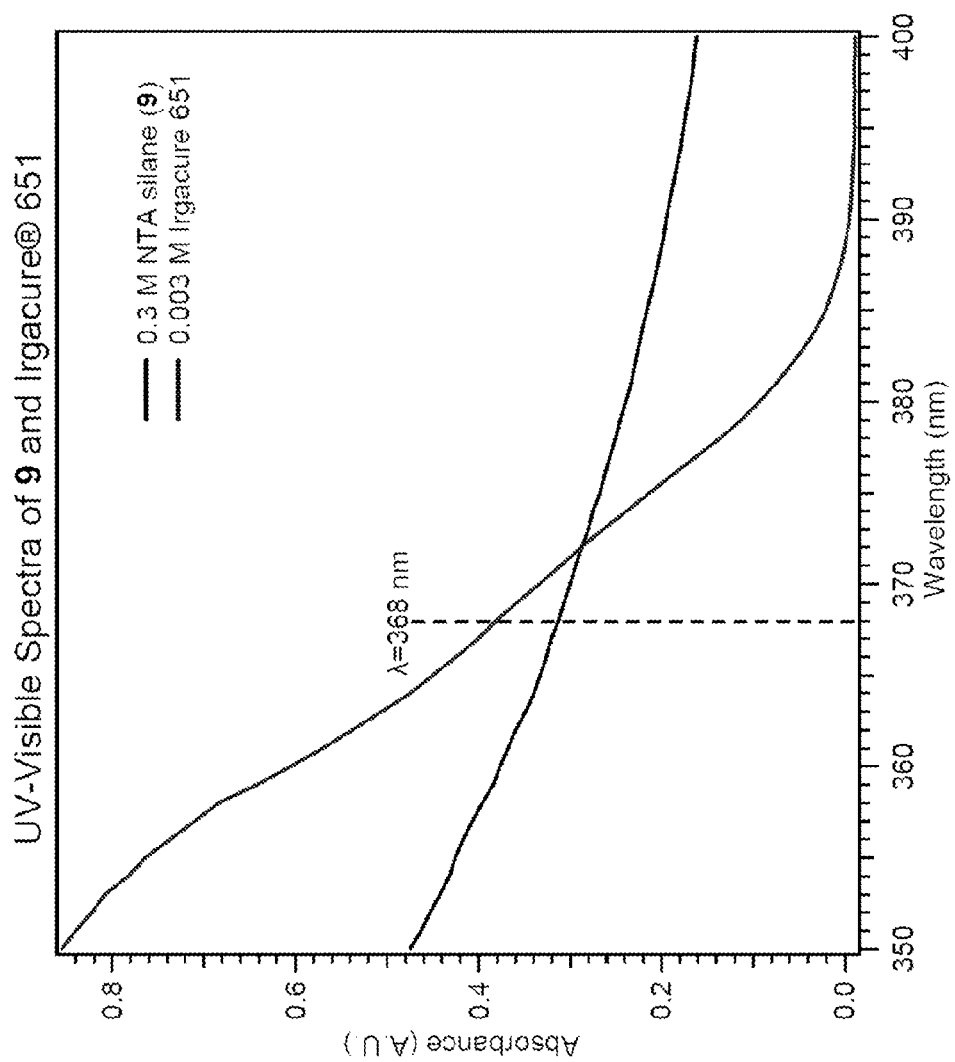
FIG. 10 is a graph illustrating a UV-visible spectra of 0.3 M NTA silane 9 in chloroform (black line) and 0.003 M Irgacure® 651 in chloroform (blue line).
Figure 11A:
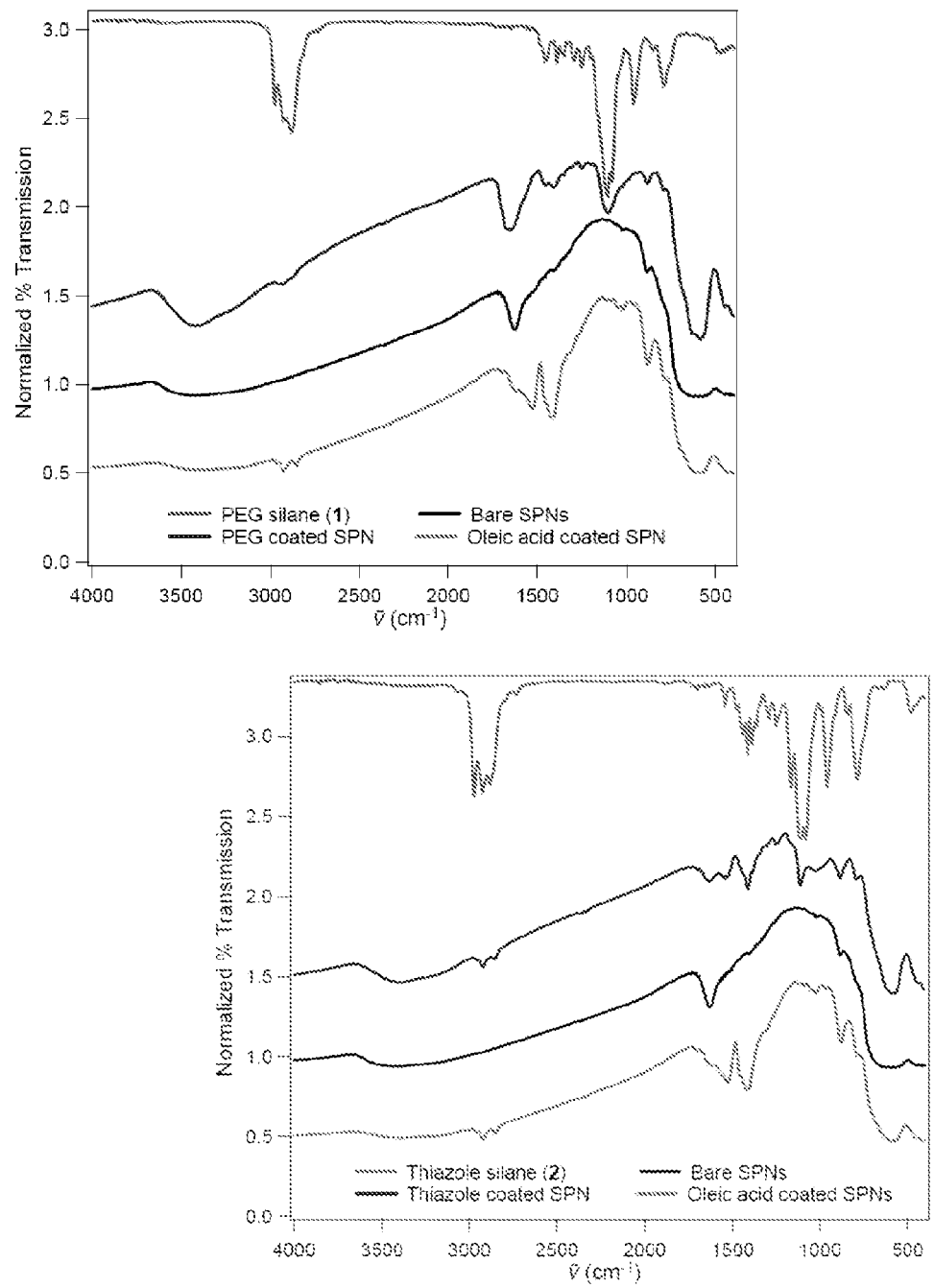
FIGS. 11A-E are a set of graphs illustrating FT-IR spectroscopic analysis of silane-coated SPNs for triethoxysilanes 1-10. Silane coatings were verified by comparing FT-IRs of silane coated SPNs to those of the pure silane and bare SPNs. For example, in FIG. 11C, the spectrum SPN-6 shares peak overlaps with bare SPNs and silane 6 spectra.
Figure 11B:
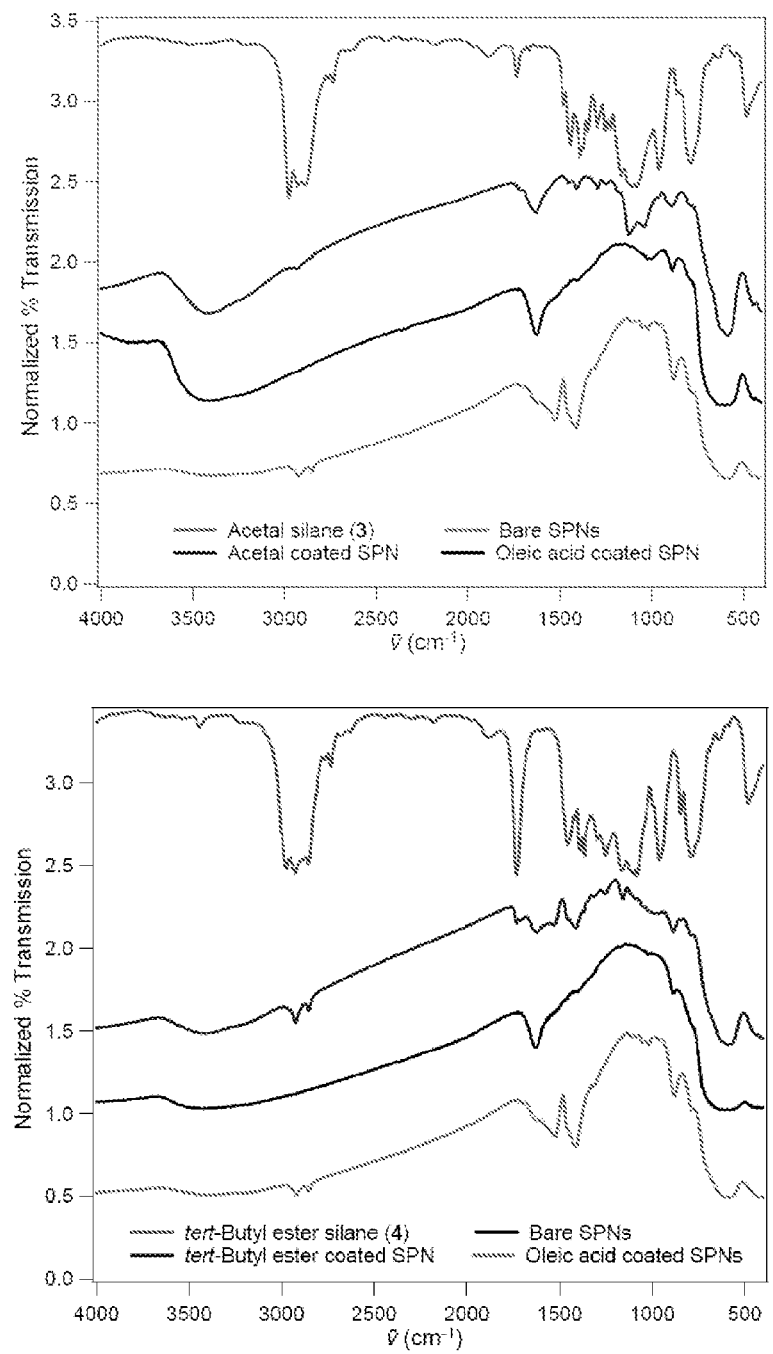
Figure 11C:
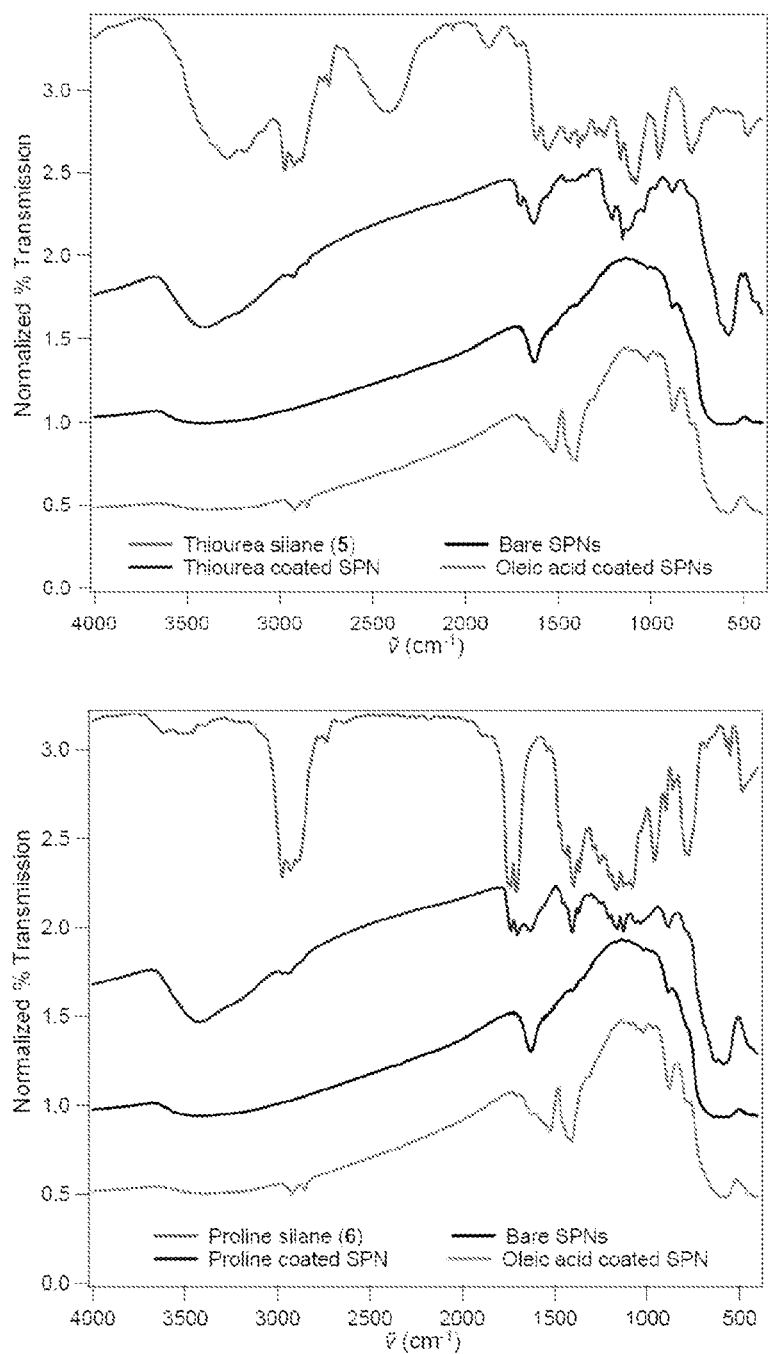
Figure 11D:
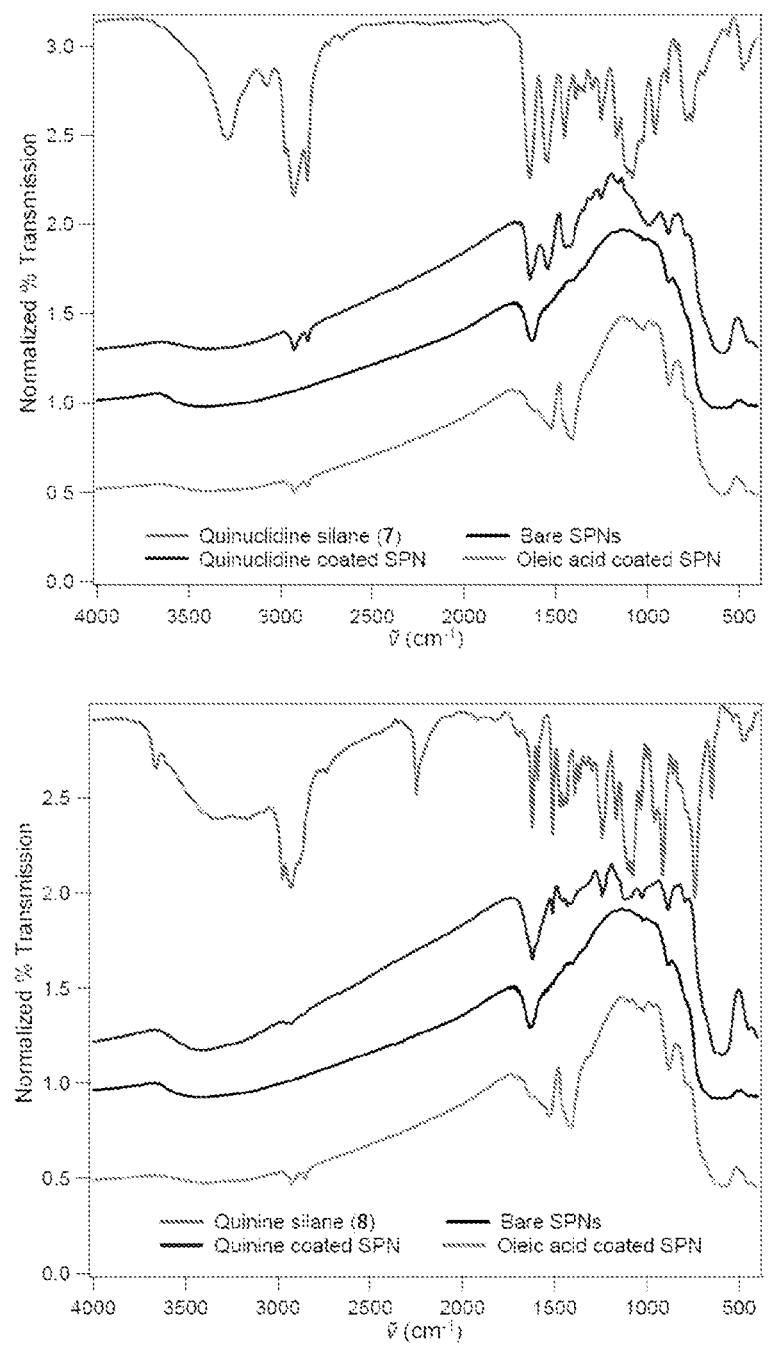
Figure 11E:
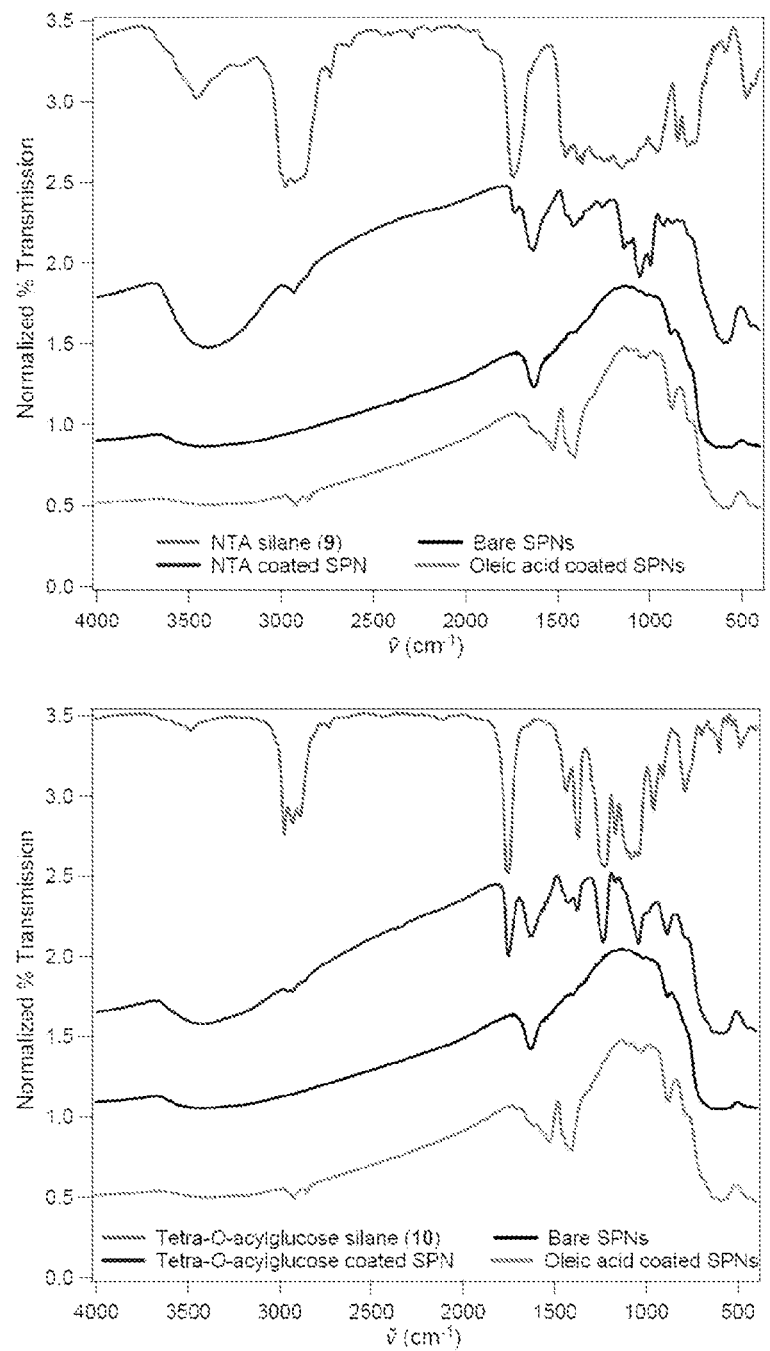

FIG. 10 shows an overlay of the UV-visible spectra of silane 9 (0.3 M) and the Irgacure® 651 photoinitiator (0.003 M). At 368 nm, $\lambda_{max}$ for the blacklight used to drive the thiol-ene reaction, there is some overlap of the absorption bands of the photoinitiator and product. This spectral overlap is believed to be a factor that prevents the reaction of MPTES (0.5 mmol) and (S)-tert-butyl-2-di(tert-butyloxycarbonylmethyl)amino-3-(pent-4-enoyloxy)pro-panoate from reaching completion. The other contributing factor is thought to be the increase in the solution viscosity of the reaction as it proceeds, which limits mass transport.

Example 8

Illustrative Methods and Materials Useful for Nanoparticle Synthesis and Silane Surface Coating Procedures 8.1—Preparation of Oleic Acid-Coated $Fe_3O_4$ Superparamagnetic Nanoparticles (SPNs).

Core magnetite SPNs were synthesized by the method previously described.₁ Briefly, 1 mL of an aqueous 3.0 M $FeCl_2$, 2 M HCl solution was mixed with 4 mL of 1.5 M $FeCl_3$, 2 M HCl on a magnetic stir plate at R.T. The iron chloride solution was then slowly titrated dropwise with 50 mL of 1.05 M $NH_4OH$ over a period of about 30 min, producing a deep black particle suspension. The superparamagnetic magnetite nanoparticles were separated using a hand-held neodymium rare-earth magnet and washed three times with water, three times with acetone, and then air-dried for at least 3 h. The collected particles were crushed, weighed and placed in a screw-cap glass vial. An equal weight of oleic acid was added to the vial along with 1 mL ethyl acetate per 0.1 g SPNs. The vial was capped and sonicated for 2 h at 60° C. The suspension was cooled, and the particles were magnetically separated, washed three times with excess ethyl acetate, three times with methanol, and then dried under vacuum. The final product was crushed to yield a black/dark brown powder.

8.2—General Procedure for Functionalizing $Fe_3O_4$ SPNs with Triethoxysilanes 1-10.

The goal of these experiments was simply to determine whether the triethoxysilanes 1-10 could be covalently attached to magnetite SPN surfaces and detected. Because we were not concerned with the relative surface reactivities of the silanes, the amount of silane used in the reaction was not tightly controlled. In most cases, the triethoxysilanes were made on ≥1 mmol scale, and 1 mmol was used to coat the SPNs. In a few cases, <1 mmol was synthesized, and all of the product was used to coat the SPNs.

Oleic acid-coated SPNs (120 mg), and either toluene or dioxane (60 mL), passed over $MgSO_4$ just prior to use, were added to a hot, oven-dried 100 mL round bottom flask. The flask was immediately capped and purged with argon for 5 min. The flask was then placed in an ultrasonication bath at R.T. and sonicated for 20 min to redisperse the oleic acid-coated SPNs. Then a stir bar was quickly added to the flask, which was immediately capped and purged 5 min with argon while vigorously stirring the particle suspension to prevent the SPNs from sticking to the stir bar. An argon balloon was placed on the flask and a triethoxysilane (0.4 to 1 mmol; see Table 1 for exact quantity of added silane) was added to the flask dropwise. The flask was placed in a 75° C. oil bath and heated for 24 h with vigorous stirring. The stir bar was removed and the particles were separated using a hand-held rare-earth magnet, washed three times with either diethyl ether or $CHCl_3$, and then dried under vacuum.

Example 9

Nanoparticle Spectroscopic Data 9.1—Elemental Analysis of Silane Loadings on Coated SPNs.

All triethoxysilanes used to coat the SPNs contained at least one sulfur atom present in the thioether bridge formed during synthesis of the silane. This allowed quantification of silane loadings on coated SPNs by sulfur elemental analysis. The experimentally-determined loadings are given in Table 1. Nearly all of the thiol-ene reactions used to produce these silanes reached ≥98% conversion. The crude products contained virtually no MPTES, which, if present, could bind to the surface and contribute to the measured sulfur content. Hence, for the reactions with >98% reactant conversions, we have assumed that the measured SPN sulfur content of the silane-coated particles derived only from the functional triethoxysilane. For the two cases in which the reactions reached only 94% or 96% conversion (6, 9), we have assumed that the percentage of the measured sulfur content that is attributable to surface-bound functional triethoxysilane is at best equal to the percent purity of the as-synthesized crude silane.

TABLE 1

Triethoxysilane loadings on SPNs.a

| Coated silane | Quantity used (mmol) | Silane loading (mmol/g SPN) |
|---|---|---|
| 1 | 1.0 | 0.23 |
| 2 | 1.0 | 0.34 |

TABLE 1-continued

Triethoxysilane loadings on SPNs.a

| Coated silane | Quantity used (mmol) | Silane loading (mmol/g SPN) |
|---|---|---|
| 3 | 1.0 | 0.79 |
| 4 | 1.0 | 0.16 |
| 5 | 1.0 | 0.31 |
| 6 | 0.5 | 0.23b |
| 7 | 0.4 | 0.27 |
| 8 | 1.0 | 0.27 |
| 9 | 0.5 | 0.13c |
| 10 | 1.0 | 0.15 | aLoadings determined by sulfur elemental analysis.
bSilane loading assuming 94% of the SPN sulfur content is from the functional silane and the rest from MPTES.
cSilane loading assuming 90% of the SPN sulfur content is from the functional silane and the rest from MPTES.

9.2—FT-IR Spectroscopic Analysis of Silane-Coated SPNs.

FIGS. 11A-E depict the FT-IR spectroscopic analysis of silane-coated SPNs for triethoxysilanes 1-10. FT-IR spectra of silane-coated SPNs pressed into KBr pellets were obtained to confirm that silanes had been immobilized on the particle surfaces. FIGS. 11A-E depict overlaid FT-IR spectra of the pure silanes, silane-coated SPNs, oleic acid-coated SPNs, and bare magnetite SPNs. The spectra verify that all of the triethoxysilanes 1-10 were successfully immobilized onto the surface of oleic-acid coated SPNs. A key indication that silanes have been covalently immobilized on the nanoparticle surface is the presence of a new Si—O—Si stretching vibration between 1060 and 1140 $cm_{-1}$.

9.3—Magnetic Properties of SPNs.

Figure 12:
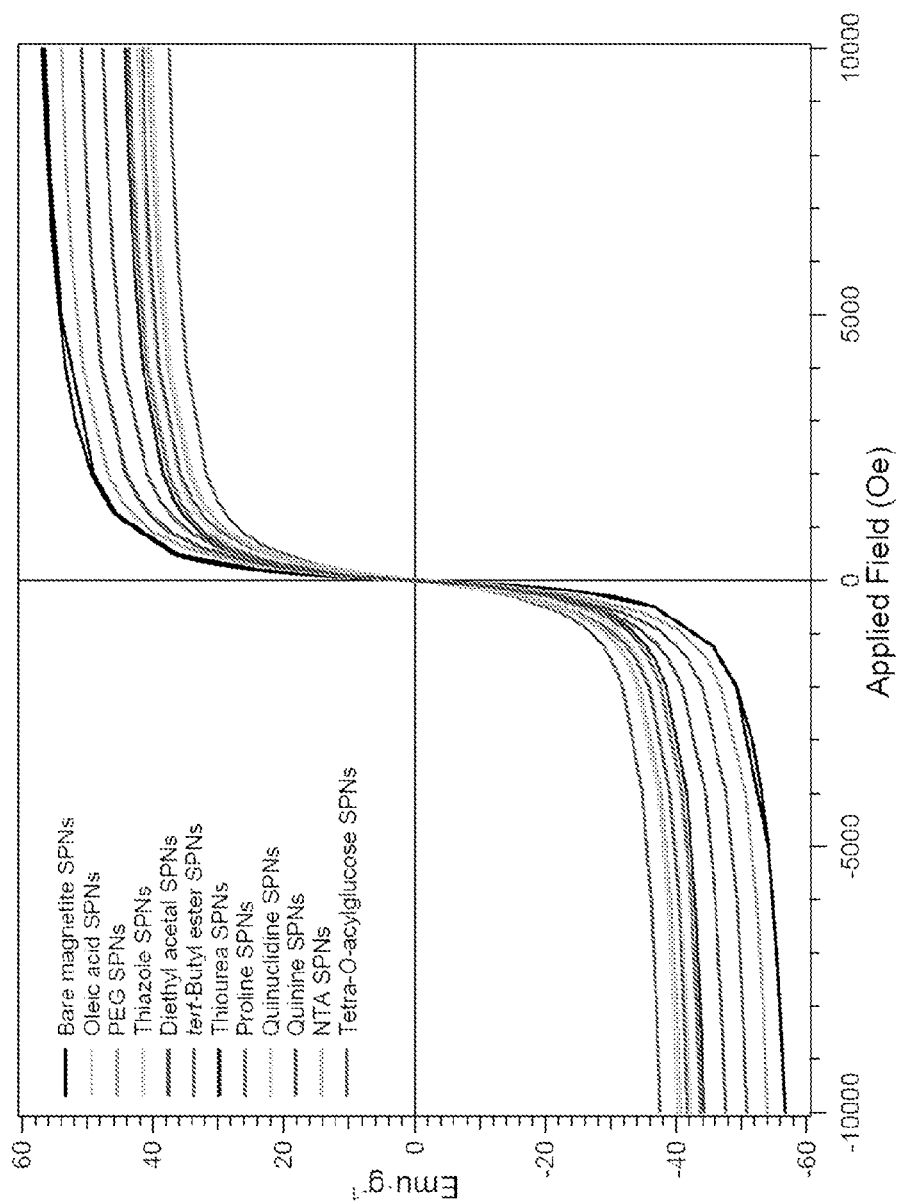
FIG. 12 is a graph illustrating magnetic hysteresis curves of various synthesized SPNs. All particles have small coercivities (6-14 Oe), indicating that they are superparamagnetic. The saturation magnetizations are large (>37 emu/g), thus, the particles are strongly attracted to magnetic fields produced by hand-held rare earth magnets.

The magnetic properties of the synthesized SPNs were measured at R.T. on a supercritical quantum interference device (SQUID). FIG. 12 shows magnetic hysteresis curves for all of the SPNs: the bare magnetite, the oleic acid-coated particles, and the silane-modified SPNs. All of the particles exhibit low coercivity, <20 Oe, indicating that they are superparamagnetic. Both the coated and uncoated particles have excellent saturation magnetizations, >34 emu/g, which means they are strongly attracted to magnetic fields produced by standard rare-earth magnets.

9.4—Transmission Electron Microscopy (TEM) of SPNs.

Figure 13:
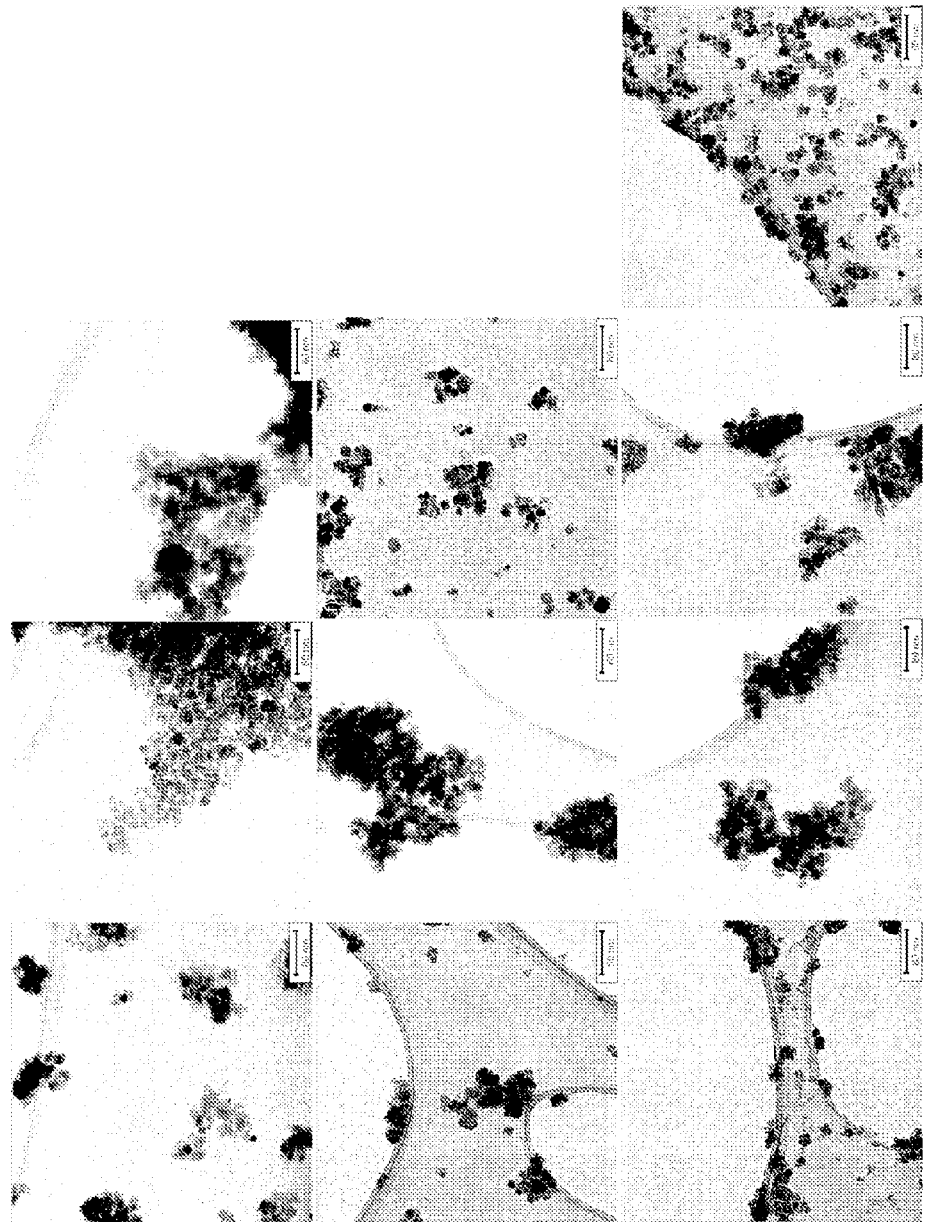
FIG. 13 is a collection of TEM images of a) PEG SPNs, 1, b) thiazole SPNs, 2, c) aectal SPNs, 3, d) tert-butyl ester SPNs, 4, e) thiourea SPNs, 5, f) proline SPNs, 6, g) quinuclidine SPNs, 7, h) quinine SPNs, 8, i) NTA SPNs, 9, j) tetra-O-acylglucose, 10, SPNs.
Figure 15:
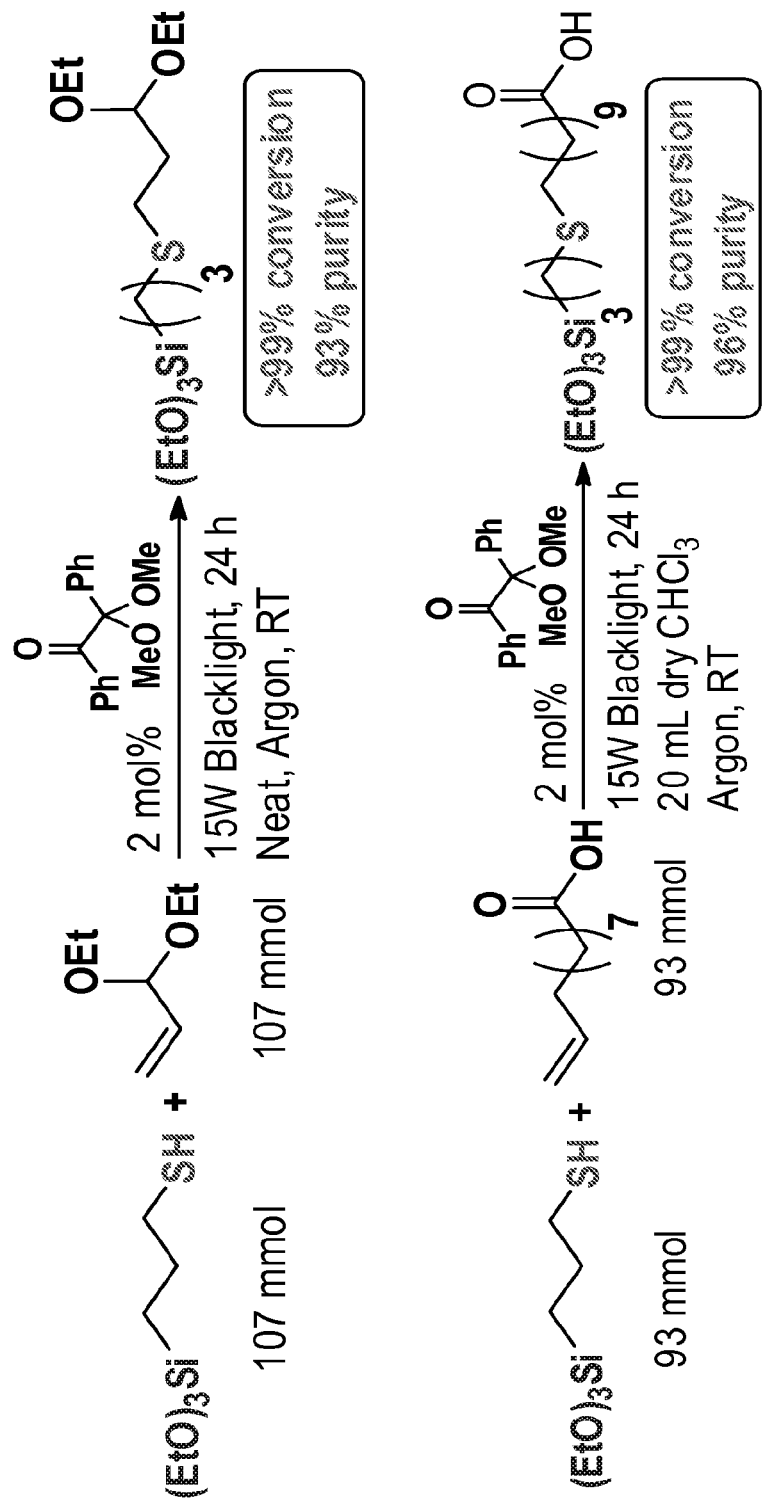
FIG. 15 illustrates examples of large-scale synthesis of two silanes and their measured crude conversion and purity percentages.
Figure 16:
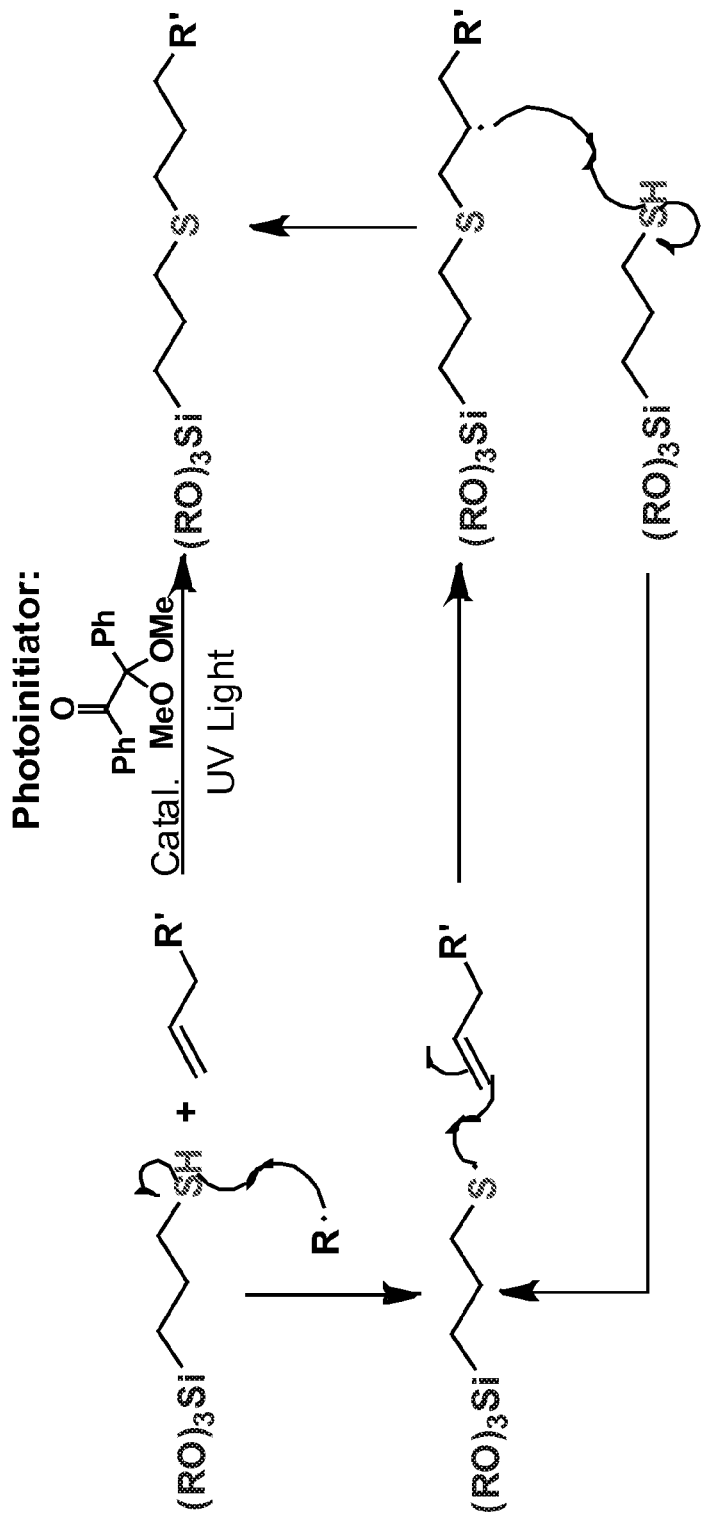
FIG. 16 is an illustrative example of a photoinitiated thiol-ene reaction cycle as applied to trialkoxysilane synthesis.

The TEM images in FIG. 13 show silane-coated SPNs ranging in size from ~10 to 25 nm. This polydispersity is expected from the protocol that was used to prepare these $Fe_3O_4$ nanoparticles. Single particles, clusters and large aggregates are typically present. We did not systematically investigate the reasons for the varying extent of particle aggregation, because many factors can influence this process and some are interdependent. These factors include: a) the composition of the surface coating; b) the surface coverage of the silane coating; c) the uniformity of silane coating; d) interactions between the particles, which are solvent-dependent; e) the dispersing solvent; and f) the cleanliness and surface charge of the carbon grids onto which the particle suspensions are deposited for TEM analysis.

Example 10

Illustrative Methods and Materials Useful for Trialkylborane Initiated Thiol-ene Reactions Embodiments of the invention involve catalyzing thiol-ene reactions by using catalytic amounts of triethylborane and a large excess of molecular oxygen or air. Illustrative reactions are typically run in the following manner. One-to-one equimolar amounts of the thiol and alkene or two-to-one molar ratio of thiol to alkyne are added to a cooled flame dried flask. The reaction mixture is purged several times with an inert gas by pulling a vacuum and then backfilling to remove all oxygen. Next, 5-10 mol % triethylborane is injected into the flask and the flask is opened to the ambient environment for 5 mins to expose the neat reaction mixture to air. The reaction is then recapped and stirred for 24-48 h.

The triethylborane/oxygen initiator system has many of the same advantages as simple thermo and photoinitiators. First, the thiol-ene reactions can be run neat with this protocol using the same inexpensive starting silanes used in other thermal or photoinitiated thiol-ene reactions. This obviates the need for environmentally unfriendly solvents. Second, reactions typically reach >99% conversion and the crude products purities are often >93%. Third, product purity can be improved post-reaction simply by pulling a vacuum on the crude products because triethylborane and many of its byproducts are volatile. Fourth, the reaction has good functional group tolerance. Finally, the biggest advantage of this initiation system is that the thiol-ene reaction can be initiated simply be exposing the triethylborane to air at room temperature. This removes the need for constant heating, cooling, or irradiation of the reactants.

Figure 17:
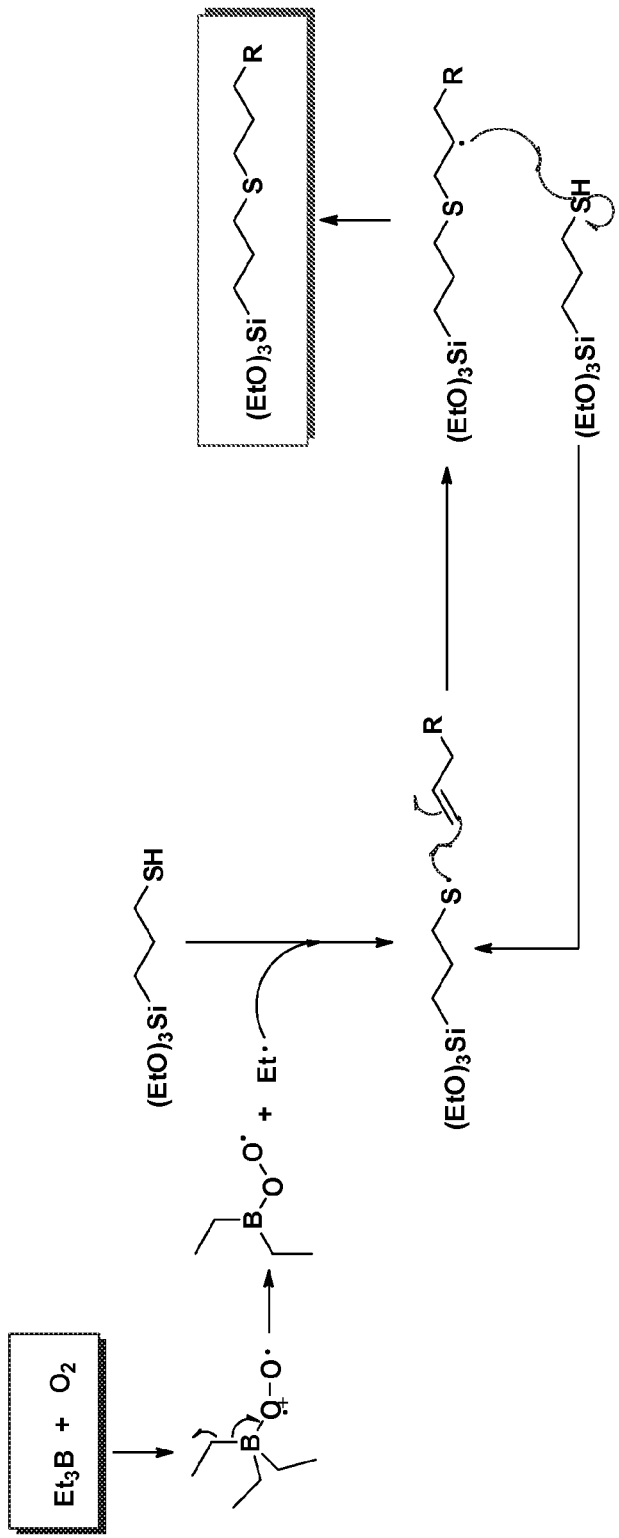
FIG. 17 shows a proposed mechanism for trialkylborane and oxygen initiated thiol-ene reactions.
Figure 18:
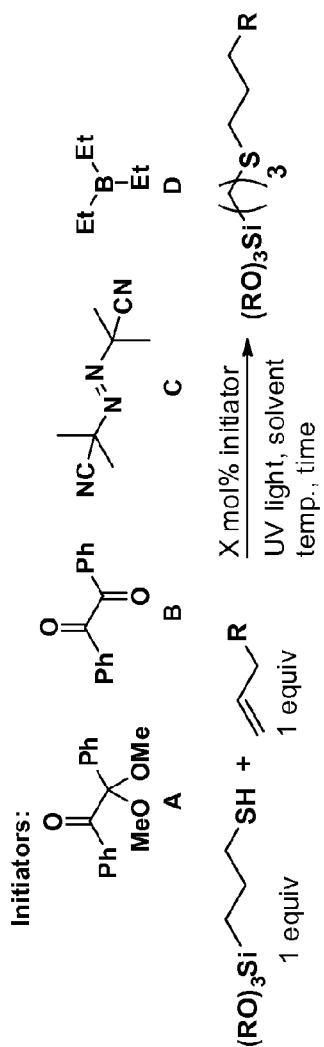
FIG. 18 shows schematic of the chemical reactants and associated conditions for and data from thiol-ene reactions catalyzed using Norish type I/II photoinitiators (molecules A and B), a thermal initiator (C), or triethylborane/oxygen (D). UV light sources for all photoinitiated reactions were carried out with a 15 W blacklight ($\lambda$max=368 nm). Triethylborane reactions were setup under backfilled argon flasks and then exposed to air for 5 min to initiate reactions.
Figure 20:
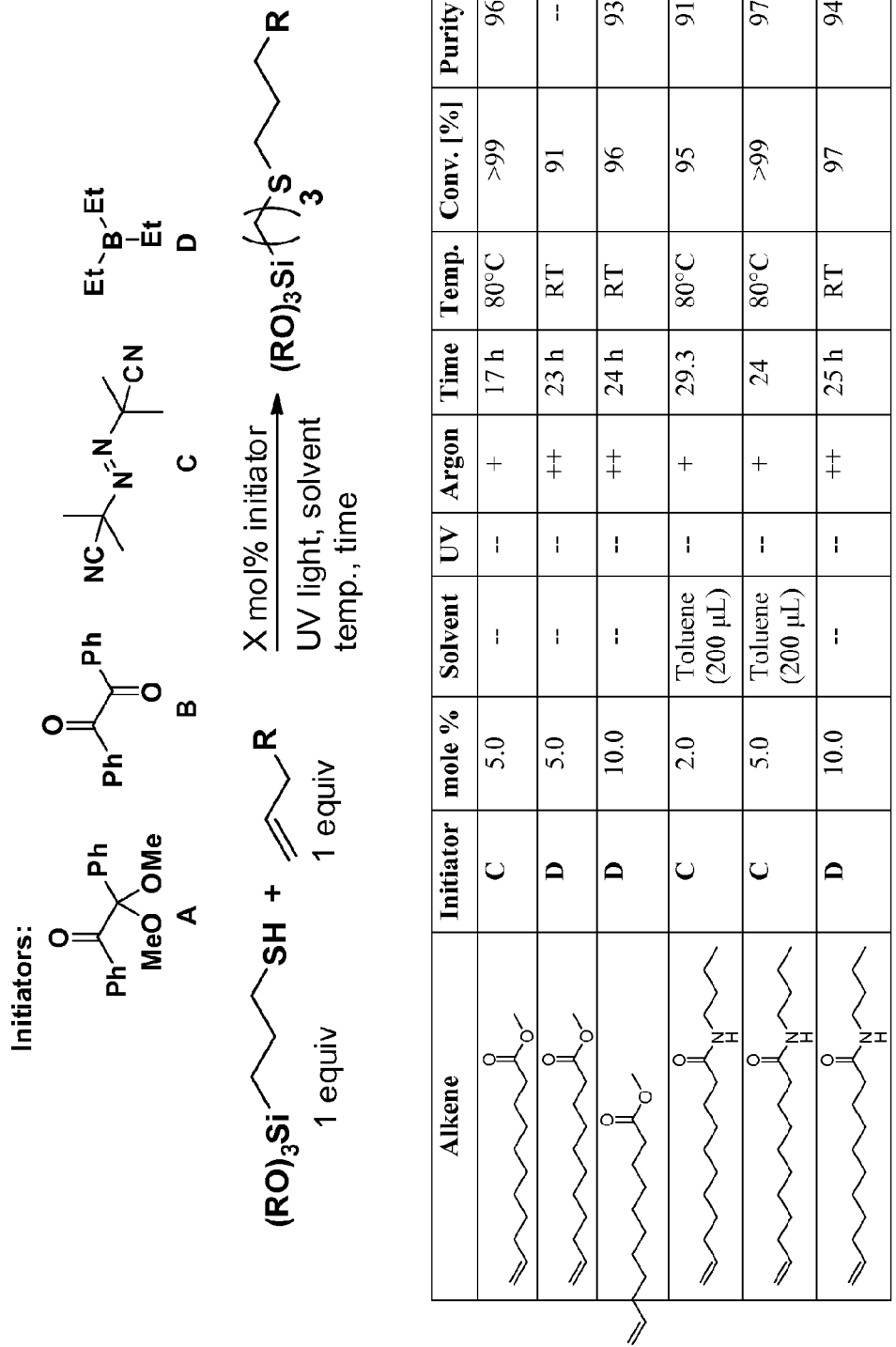
FIG. 20 shows schematic of the chemical reactants and associated conditions for and data from thiol-ene reactions catalyzed using Norish type I/II photoinitiators (molecules A and B), a thermal initiator (C), or triethylborane/oxygen (D). UV light sources for all photoinitiated reactions were carried out with a 15 W blacklight ($\lambda$max=368 nm). Triethylborane reactions were setup under backfilled argon flasks and then exposed to air for 5 min to initiate reactions.
Figure 21:
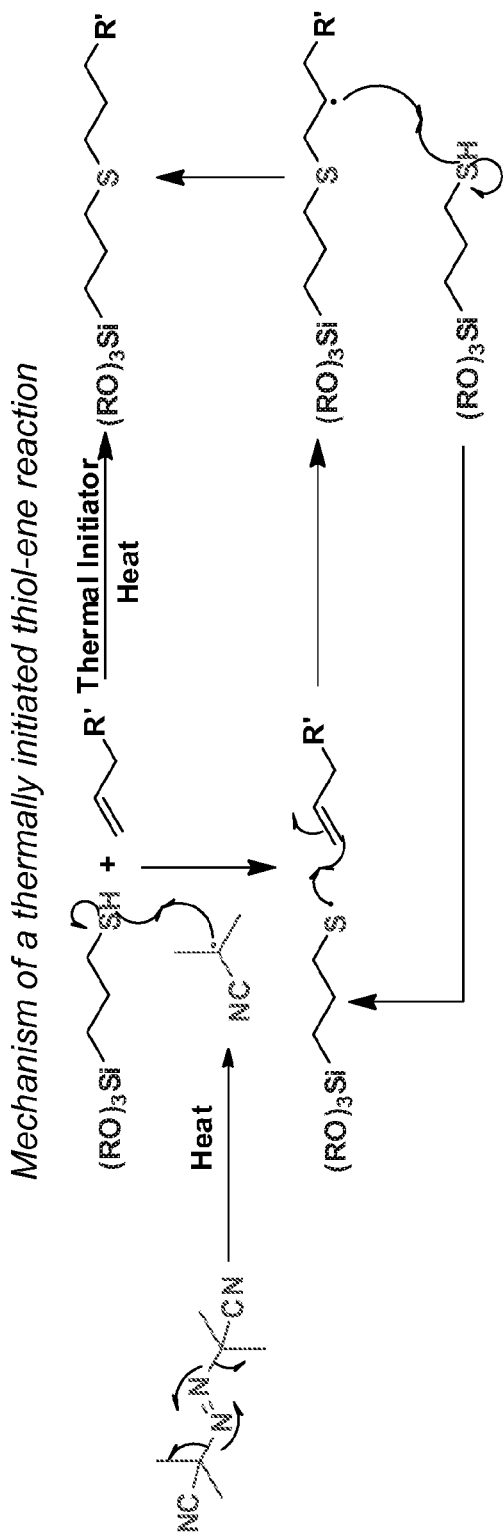
FIG. 21 shows a proposed mechanism for thermally initiated thiol-ene reactions.
Figure 22:
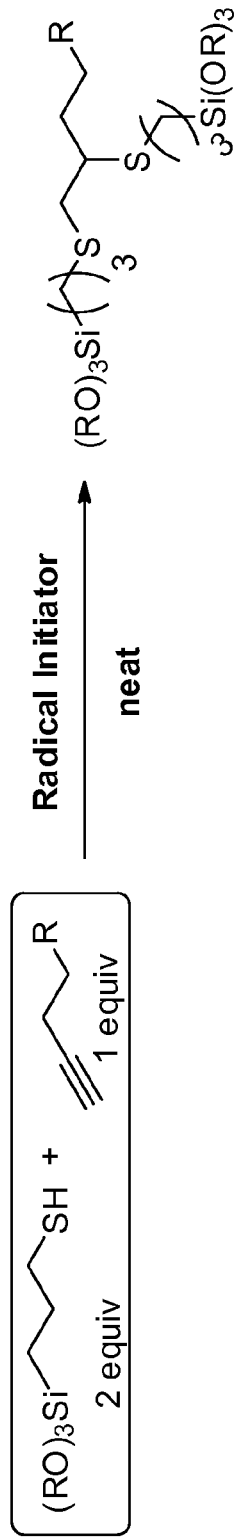
FIG. 22 is a schematic illustrating a general methodology of the present invention for synthesis of trialkoxysilanes when using an alkyne.

The general thiol-ene reaction mechanism is the same as for the thermal and photoinitiated reactions. The only difference with this initiation methodology is that how the initiating radicals are formed. Without being bound by a particular theory of mechanism of action, the proposed mechanism for radical generation from the reaction of trialkylborane and oxygen is shown in FIG. 17: The tables of FIGS. 18-20 show data on thiol-ene reactions catalyzed using Norish type I/II photoinitiators (molecules A and B), a thermal imitator (C), or triethylborane/oxygen (D). UV light sources for all photoinitiated reactions were carried out with a 15 W blacklight (λmax=368 nm). Triethylborane reactions were setup under backfilled argon flasks and then exposed to air for 5 min.

This concludes the description of the illustrative embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

The invention claimed is:

1. A method for making a trialkoxysilane compound comprising a thioether, the method comprising the steps of:
   (a) forming a mixture comprising:
      a trialkoxysilane compound;
      a compound comprising a sulfhydryl moiety;
      an alkene compound or an alkyne compound; and
      a radical initiator agent;
   (b) initiating a chemical reaction in the mixture so that:
      the radical initiator agent reacts with a hydrogen atom in a first sulfhydryl moiety so as to form a thiyl radical;
      the thiyl radical reacts with the alkene or the alkyne so as to form a radical intermediate;
      the radical intermediate reacts with a hydrogen atom in a second thiol moiety so as to form a thioether;
   so that the trialkoxysilane compound comprising the thioether is made; and
the chemical reaction in (b) produces a composition of matter wherein the trialkoxysilane compound comprising the thioether has a purity of at least 90%.

2. The method of claim 1, wherein:
   the trialkoxysilane compound comprises the sulfhydryl moiety; or
   the trialkoxysilane compound is the alkene compound.

3. The method of claim 1, further comprising placing the composition of matter under a negative pressure to remove a constituent of the composition of matter having a vapor pressure higher than the trialkoxysilane compound comprising the thioether.

4. The method of claim 1, wherein the mixture does not comprise a solvent.

5. The method of claim 1, wherein:
   the mixture comprises 1:1 molar equivalents of the sulfhydryl moiety and the alkene; and/or
   the mixture comprises 2:1 molar equivalents of the sulfhydryl moiety and the alkyne.

6. The method of claim 1, wherein the mixture does not comprise a metallic catalyst agent or a chiral organic ligand.

7. The method of claim 1, wherein the activity of the radical initiator agent is initiated by light, heat or exposure to oxygen.

8. The method of claim 7, wherein the activity of the radical initiator agent is initiated by ultraviolet light and the mixture is contained in an optically transparent vessel.

9. The method of claim 1, further comprising covalently coupling the trialkoxysilane compound comprising the thioether to a surface matrix.

10. The method of claim 1, wherein the chemical reaction is performed as a one-pot synthesis.

11. A method for modifying a surface of a material comprising the steps of:
    a) forming a mixture comprising:
       a trialkoxysilane compound;
       a compound comprising a sulfhydryl moiety;
       an alkene compound or an alkyne compound; and
       a radical initiator agent;
    b) initiating a chemical reaction in the mixture so that:
       the radical initiator agent reacts with a hydrogen atom in a first sulfhydryl moiety so as to form a thiyl radical;
       the thiyl radical reacts with the alkene or the alkyne so as to form a radical intermediate;
       the radical intermediate reacts with a hydrogen atom in a second thiol moiety so as to form a thioether linkage;
       so that a trialkoxysilane compound comprising the thioether is made; and
    c) covalently coupling the trialkoxysilane compound comprising the thioether to the surface so that so that the surface of the material is modified.

12. The method of claim 11, wherein the surface comprises a metal, metal oxide composition, a polymer composition or a plastic composition.

13. The method of claim 11, wherein the alkene, the alkyne or the compound comprising a sulfhydryl moiety is covalently linked to a pendant group comprising one or more of an imaging agent, a surface wetting agent, a water repelling agent, an antimicrobial agent, a therapeutic agent, a ligand or a catalytic agent, so that the surface is modified by having the functional group coupled thereto.

14. The method of claim 11, wherein the pendant group comprises one or more of a thiazolium carbene, a thiourea, carboxylic acid, an aldehyde, a fluorophore, a lectin, a lipid, a carbohydrate, a polymer, polyol, a polynucleotide or a polypeptide.

15. The method of claim 11, wherein the surface is hydroxylated and the trialkoxysilane compound comprising the thioether is covalently coupled to the surface via an oxane bond.

16. The method of claim 11, wherein the chemical reaction in (b) produces the trialkoxysilane compound comprising the thioether having a purity of between 80%-99%.

17. The method of claim 11, wherein the trialkoxysilane compound comprising the thioether to the surface is coupled to the surface of the substrate following step (b) in the absence of any distillation or chromatography purification steps.

18. The method of claim 11, wherein the trialkoxysilane compound and the compound comprising the sulfhydryl moiety are different chemical compounds.

19. The method of claim 11, wherein the mixture comprises a solvent in an amount less than 5 wt %.

20. A material having a surface modified according to the method of claim 11.

* * * * *